US011937828B2

(12) United States Patent
Takizawa et al.

(10) Patent No.: US 11,937,828 B2
(45) Date of Patent: Mar. 26, 2024

(54) ENDOSCOPE TREATMENT DEVICE

(71) Applicant: OLYMPUS MEDICAL SYSTEMS CORP., Tokyo (JP)

(72) Inventors: Naoki Takizawa, Hirosaki (JP); Motoi Satake, Kokubunji (JP)

(73) Assignee: Olympus Medical Systems Corp., Tokyo (JP)

( * ) Notice: Subject to any disclaimer, the term of this patent is extended or adjusted under 35 U.S.C. 154(b) by 259 days.

(21) Appl. No.: 17/575,883

(22) Filed: Jan. 14, 2022

(65) Prior Publication Data
US 2022/0233197 A1 Jul. 28, 2022

Related U.S. Application Data

(60) Provisional application No. 63/141,620, filed on Jan. 26, 2021.

(51) Int. Cl.
*A61B 17/128* (2006.01)
*A61B 17/122* (2006.01)

(52) U.S. Cl.
CPC ...... *A61B 17/1285* (2013.01); *A61B 17/1227* (2013.01)

(58) Field of Classification Search
CPC .............. A61B 17/122; A61B 17/1227; A61B 17/1285
See application file for complete search history.

(56) References Cited

U.S. PATENT DOCUMENTS 3,958,576 A * 5/1976 Komiya ................ A61B 17/10
24/537
4,367,746 A * 1/1983 Derechinsky ...... A61B 17/1285
606/142
(Continued)

FOREIGN PATENT DOCUMENTS

EP 1547529 A1 6/2005
JP 2002-191609 A 7/2002
(Continued)

OTHER PUBLICATIONS

International Search Report (partial translation) issued in corresponding International Patent Application No. PCT/JP2022/002771, dated Apr. 19, 2022.
(Continued)

*Primary Examiner* — Ryan J. Severson
(74) *Attorney, Agent, or Firm* — Morgan, Lewis & Bockius LLP

(57) ABSTRACT

A clip device includes a tube and a clip having a first arm portion and a second arm portion, and an engagement mechanism including a stepped connector and a hooking structure, and configured to connect to the clip. The stepped connector includes an engaging region connecting two side regions, a width of the engaging region of the stepped connector is smaller than a width of a first of the two side regions of the stepped connector. The hooking structure includes two lateral surfaces connected by a hook surface, and a surface of the engaging region of the stepped connector engages with the hook surface of the hooking structure and each of the two side regions of the stepped connector are adjacent to respective one of the two lateral surfaces of the hooking structure.

20 Claims, 17 Drawing Sheets

(56) References Cited

U.S. PATENT DOCUMENTS

| | | | | |
|---|---|---|---|---|
| 5,242,456 | A * | 9/1993 | Nash | A61B 17/0218 606/151 |
| 5,569,274 | A * | 10/1996 | Rapacki | A61B 18/1442 606/151 |
| 5,766,189 | A * | 6/1998 | Matsuno | A61B 17/122 606/139 |
| 6,814,742 | B2 * | 11/2004 | Kimura | A61B 17/1285 606/151 |
| 7,727,247 | B2 * | 6/2010 | Kimura | A61B 17/1285 606/142 |
| 7,854,739 | B2 * | 12/2010 | Satake | A61B 17/1285 606/151 |
| 8,152,824 | B2 * | 4/2012 | Kimura | A61B 17/1285 24/537 |
| 8,157,824 | B2 * | 4/2012 | Kimura | A61B 17/1285 24/537 |
| 8,172,859 | B2 * | 5/2012 | Matsuno | A61B 17/1285 606/151 |
| 8,348,964 | B2 * | 1/2013 | Kimura | A61B 17/1222 606/157 |
| 8,444,660 | B2 * | 5/2013 | Adams | A61B 17/122 606/157 |
| 8,465,501 | B2 * | 6/2013 | Matsuoka | A61B 17/1222 606/157 |
| 8,529,585 | B2 * | 9/2013 | Jacobs | A61B 17/1285 606/151 |
| 8,672,952 | B2 * | 3/2014 | Suzuki | A61B 17/320016 606/142 |
| 9,138,234 | B2 * | 9/2015 | Li | A61B 17/122 |
| 9,662,113 | B2 * | 5/2017 | Satake | A61B 17/1285 |
| 9,687,248 | B2 * | 6/2017 | Satake | A61B 17/122 |
| 9,949,740 | B2 * | 4/2018 | Satake | A61B 17/122 |
| 10,524,801 | B2 * | 1/2020 | Muyari | A61B 17/122 |
| 10,828,035 | B2 * | 11/2020 | Maekubo | A61B 17/1285 |
| 11,141,166 | B2 * | 10/2021 | Itoh | A61B 17/1285 |
| 11,234,707 | B2 * | 2/2022 | Yu | A61B 17/122 |
| 2002/0045909 | A1 * | 4/2002 | Kimura | A61B 17/083 606/151 |
| 2005/0143767 | A1 * | 6/2005 | Kimura | A61B 50/30 606/158 |
| 2010/0217292 | A1 * | 8/2010 | Kimura | A61B 17/1285 606/157 |
| 2010/0217293 | A1 * | 8/2010 | Kimura | A61B 17/1227 606/157 |
| 2010/0217294 | A1 * | 8/2010 | Kimura | A61B 17/1227 606/157 |
| 2015/0305741 | A1 * | 10/2015 | Satake | A61B 17/1285 606/142 |
| 2018/0353183 | A1 * | 12/2018 | Maekubo | A61B 17/083 |
| 2021/0267602 | A1 * | 9/2021 | Tsuji | A61B 17/00234 |
| 2022/0233197 | A1 * | 7/2022 | Takizawa | A61B 17/1285 |
| 2022/0233198 | A1 * | 7/2022 | Yoshii | A61B 17/1285 |

FOREIGN PATENT DOCUMENTS

| | | |
|---|---|---|
| JP | 2002-360589 A | 12/2002 |
| JP | 2009-022776 A | 2/2009 |
| JP | 2010-029629 A | 2/2010 |
| JP | 5750620 B2 | 7/2015 |
| WO | 2020/095427 A1 | 5/2020 |
| WO | 2020/095428 A1 | 5/2020 |
| WO | 2020/122120 A1 | 6/2020 |

OTHER PUBLICATIONS

International Search Report (OA1) issued in corresponding International Patent Application No. PCT/JP2021/008932, dated May 11, 2021.

International Search Report (OA2) issued in corresponding International Patent Application No. PCT/JP2021/009575, dated Apr. 27, 2021.

Notice of Allowance dated Jul. 4, 2023, issued in corresponding Japanese Patent Application No. 2022-031146.

* cited by examiner

ENDOSCOPE TREATMENT DEVICE

RELATED APPLICATION DATA

This application is based on and claims priority under 35 U.S.C. § 119 to U.S. Provisional Application No. 63/141,620, filed Jan. 26, 2021, the entire contents of which are incorporated herein by reference.

FIELD OF THE INVENTION

The present invention relates to an endoscope treatment device inserted into a body and used to ligate a tissue, and more particularly, to such an endoscope treatment device with an improved clip unit.

DESCRIPTION OF THE RELATED ART

Various endoscope treatment devices have been known. One such device is a ligation device which includes a clip unit and is used to ligate openings formed in tissues or blood vessels. A conventional ligation device may include a clip unit, a treatment tool body and a connection structure configured to connect the treatment tool body to the clip unit. The clip unit is detachably mounted on a distal end of the treatment tool body. The clip unit may include a clip main body and a pressing tube which is configured to accommodate the clip main body. The clip main body includes a pair of arm portions and a middle portion disposed between proximal ends of the pair of arm portions and connecting the pair of arm portions.

The connection structure includes a hook portion disposed at the distal end of the treatment tool body. The middle portion of the clip unit is engaged with the hook portion of the connection structure. By this engagement, the clip unit is able to be advanced and retracted through the pressing tube by operating the treatment tool body. Also, the clip unit is rotatable around an axis of the pressing tube so as to adjust the positions of the pair of arm portions during the procedure of grasping the tissue.

However, the conventional connection structure between the clip unit and the treatment tool body is deficient in one or more ways. For example, the conventional connection structure lacks sufficient strength to ensure the rotating movement of the clip unit around the axis of the pressing tube when the clip unit is rotated. Also for example, the conventional connection structure lacks sufficient strength to ensure a linear movement of the clip unit in the axis direction of the pressing tube when the clip unit is pulled by a manipulation wire. As a result, the clip unit may unexpectedly come off the hook portion of the treatment tool body before the ligating procedure is successfully completed.

SUMMARY OF THE INVENTION

Accordingly, the present disclosure is directed to an endoscope treatment device and clip unit, which substantially obviate one or more of the issues due to limitations and disadvantages found in conventional endoscope treatment devices and clip units.

An object of the present disclosure is to provide a clip device, which comprises a tube having an interior volume and at least one open end; a clip including a first arm portion and a second arm portion, and wherein the clip is configured to slidably move between a retracted position in which the first and second arm portions are within the interior volume of the tube and a deployed position in which the first and second arm portions protrude from the open end of the tube; and an engagement mechanism disposed inside the tube and including a stepped connector and a hooking structure, wherein the engagement mechanism is configured to connect to the clip. The stepped connector includes an engaging region connecting two side regions, wherein a width of the engaging region of the stepped connector is smaller than a width of a first of the two side regions of the stepped connector. The hooking structure includes two lateral surfaces connected by a hook surface. A surface of the engaging region of the stepped connector engages with the hook surface of the hooking structure and each of the two side regions of the stepped connector are adjacent to respective one of the two lateral surfaces of the hooking structure.

Another object of the present disclosure is to provide an endoscope treatment device for ligaturing a living tissue, which comprises: a clip unit including first and second arm portions; and a pressing tube which is formed to be capable of accommodating the first and second are portions to make a distal end of the first arm portion and a distal end of the second arm portion approaching to each other; a linear member connected to the dip unit and provided to advance and retract the clip unit; a sheath in which the linear member is inserted so that the linear member is advanceable and retractable. The clip unit further includes an engagement mechanism disposed inside the tube and including a stepped connector and a hooking structure, wherein the engagement mechanism is configured to connect to the clip. The stepped connector includes an engaging region connecting two side regions, wherein a width of the engaging region of the stepped connector is smaller than a width of a first of the two side regions of the stepped connector. The hooking structure includes two lateral surfaces connected by a hook surface. A surface of the engaging region of the stepped connector engages with the hook surface of the hooking structure and each of the two side regions of the stepped connector are adjacent to respective one of the two lateral surfaces of the hooking structure.

Additionally, the engagement mechanism can have varying forms. In one embodiment, the stepped connector is part of the clip, and the hooking structure is connected to a manipulating line. In another embodiment, the hooking structure is part of the clip, and the stepped connector is connected to the manipulating line. In still another embodiment, the engagement mechanism includes two hooking structures, each with two lateral surfaces connected by a hook surface, and the stepped connector includes surfaces associated with two stepped connectors, each with an engaging region and two side regions, and the various features of the hooking structures and stepped connector function in a similar manner as for corresponding features in the single feature embodiments.

Additional features and advantages will be set forth in the description that follows, and in part will be apparent from the description, or may be learned by practice of the invention. The objectives and other advantages of the disclosed an endoscope treatment device and clip unit will be realized and attained by the structure particularly pointed out in the written description and claims thereof as well as the appended drawings.

BRIEF DESCRIPTION OF THE DRAWING

The following detailed description of preferred embodiments can be read in connection with the accompanying drawings in which like numerals designate like elements and in which.

Figure 1:
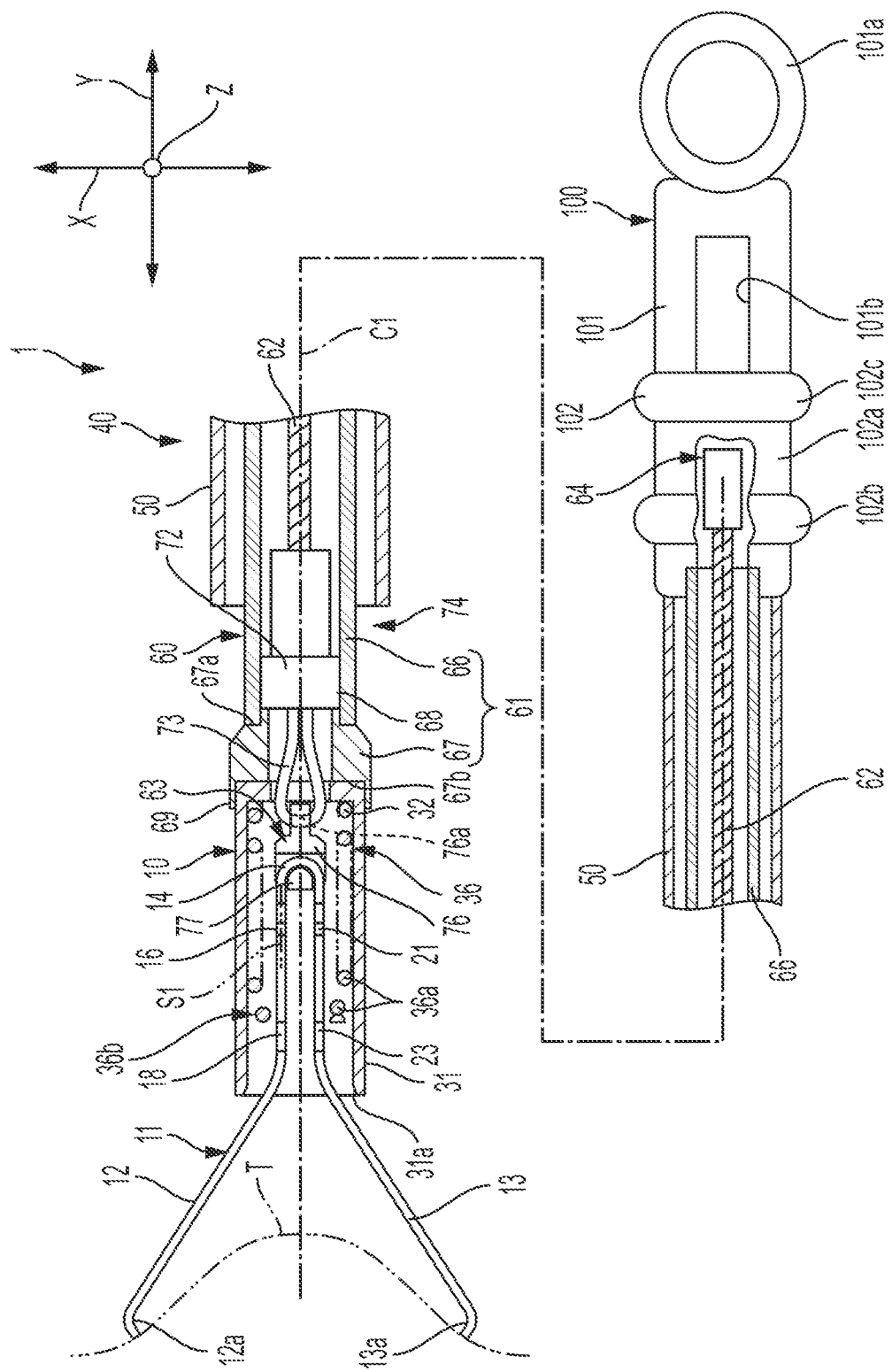
FIG. 1 is a sectional view (by cutting away a part of a side surface of the endoscope treatment device) schematically showing an endoscope treatment device in which a clip unit according to an exemplary embodiment is used.

For ease of viewing, in some instances only some of the named features in the figures are labeled with reference numerals.

DETAILED DESCRIPTION

Hereinafter, accompanying drawings, which are incorporated in and constitute a part of the specification, illustrate exemplary embodiments of the invention, and together with the general description given above and the detailed description of the exemplary embodiments given below, serve to explain the principles of the invention. Throughout all of the drawings, ratios of the thicknesses or dimensions of respective constituent elements are appropriately adjusted for clarity.

Also, it should be noted that references throughout this disclosure to the terms "distal" and "distally" are to a direction away from a manipulation portion 100 (see FIG. 1), while references to the terms "proximal" and "proximally" are to a direction towards the manipulation portion 100.

Figure 2:
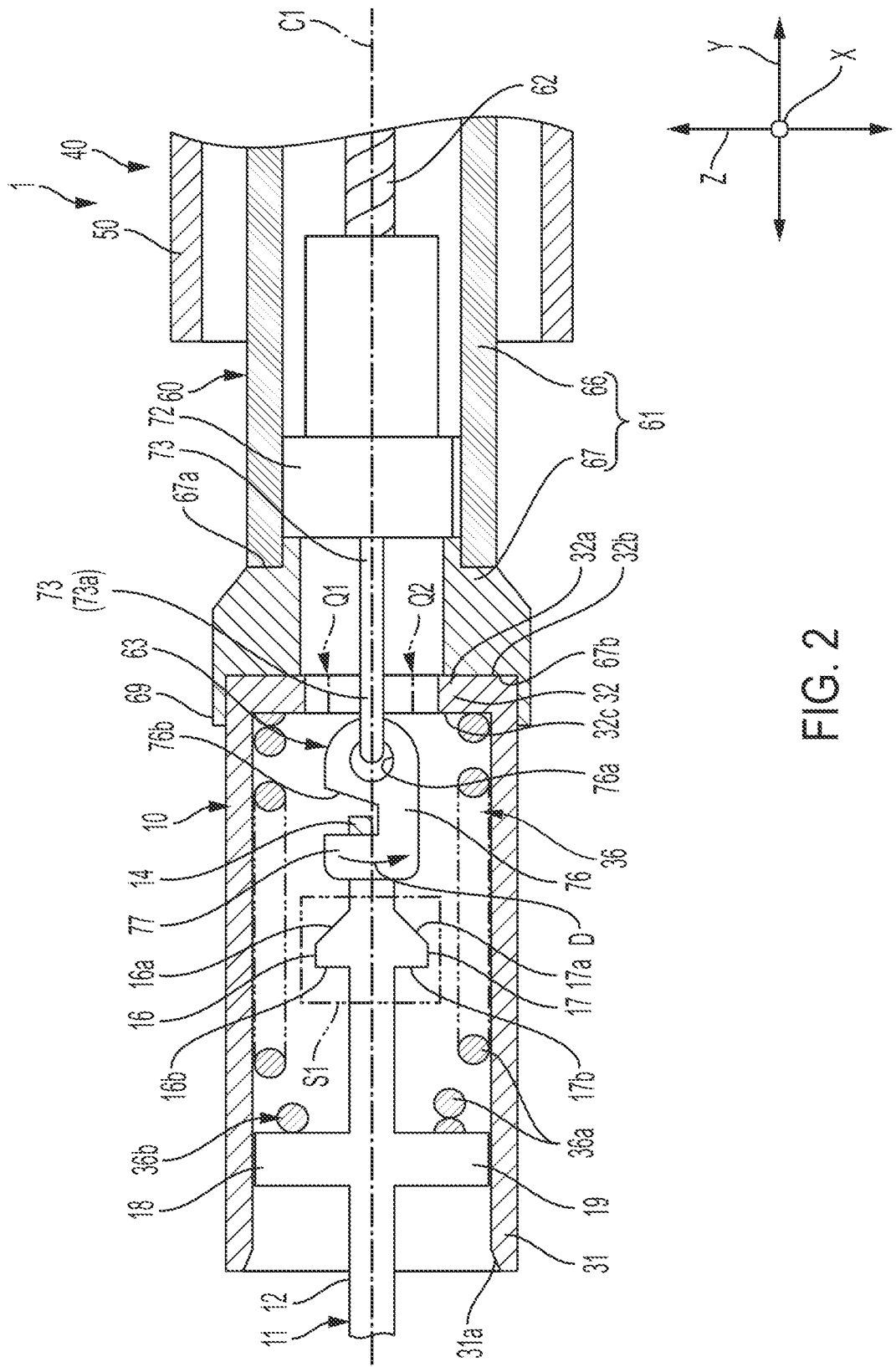
FIG. 2 is a top sectional view schematically showing the distal end of the endoscope treatment device in FIG. 1.

FIGS. 1 and 2 show an endoscope treatment device 1 as a ligation tool and includes a clip unit (hereinafter also abbreviated as a "clip") 10 and a treatment device body 40. The clip 10 can be detachably mounted on a distal end of the treatment device body 40. FIGS. 1 and 2 are sectional views passing through an axial line C1 of a pressing tube 31 to be described below.

Figure 3:
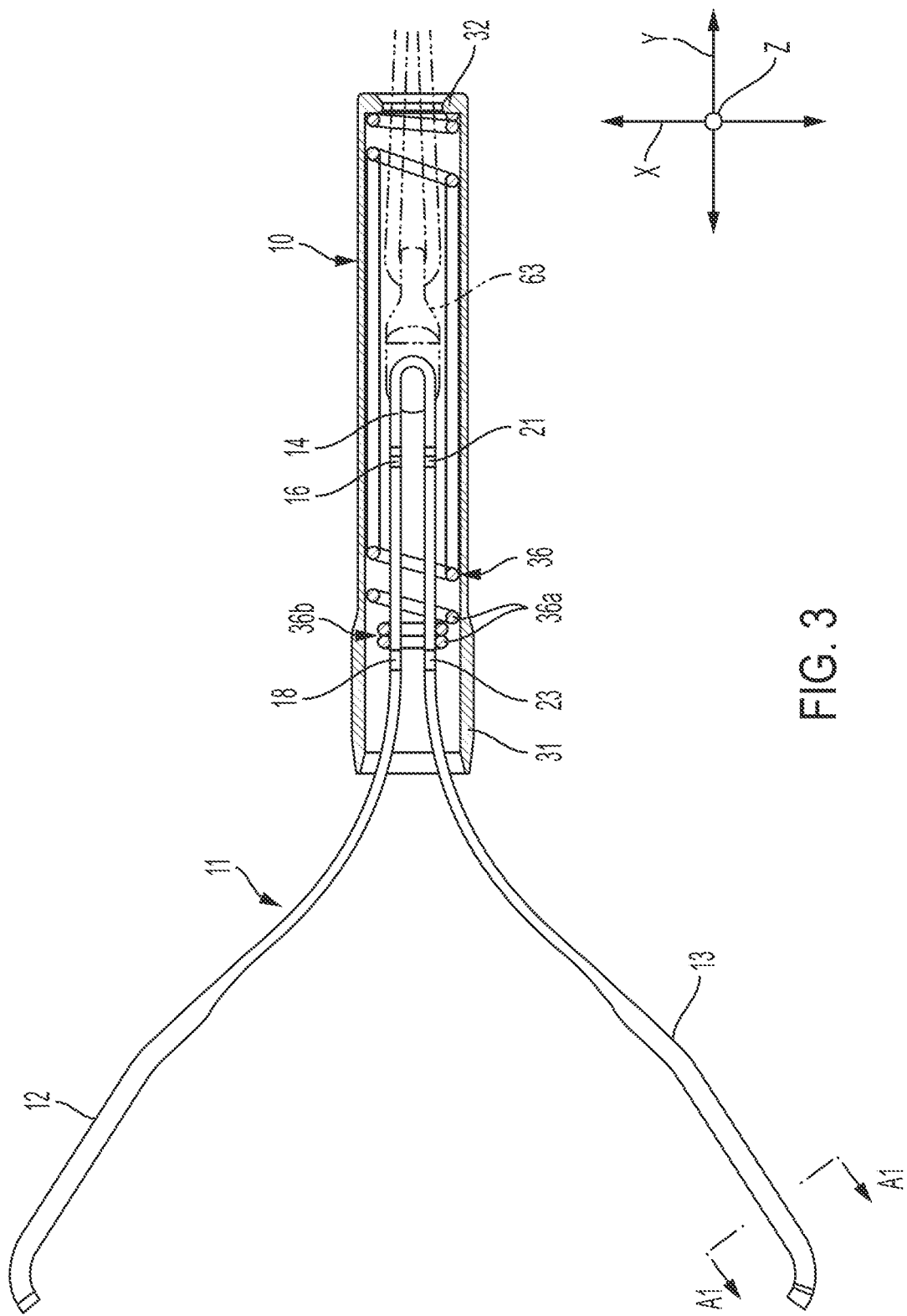
FIG. 3 is a side sectional view showing a clip unit in FIG. 1.
Figure 4:
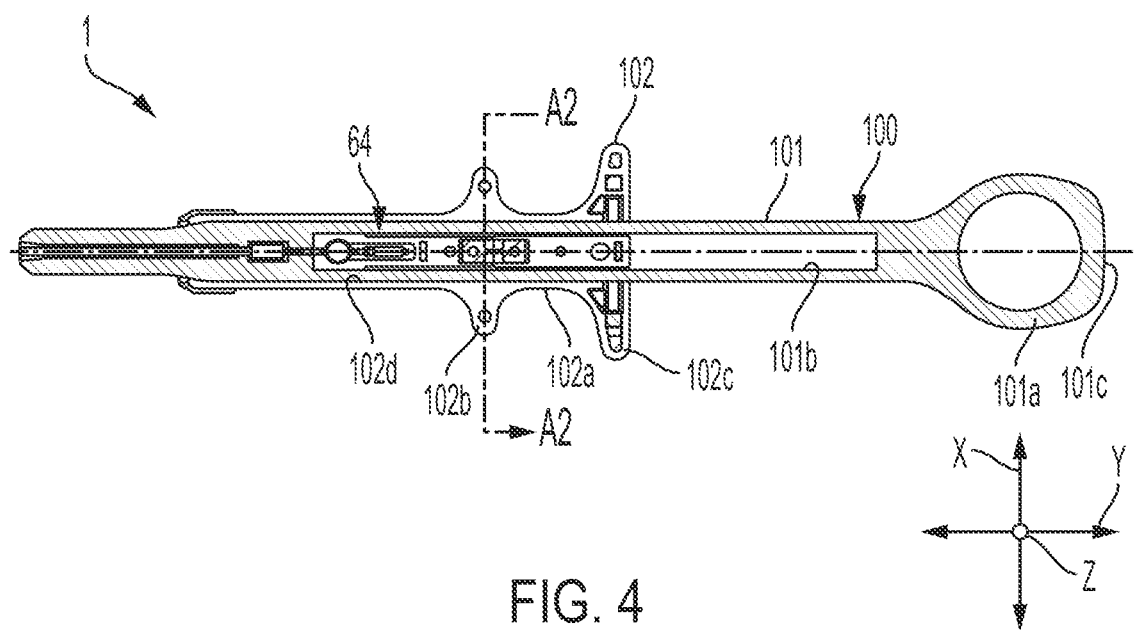
FIG. 4 is a side sectional view showing the proximal end of the endoscope treatment device in FIG. 1.
Figure 5:
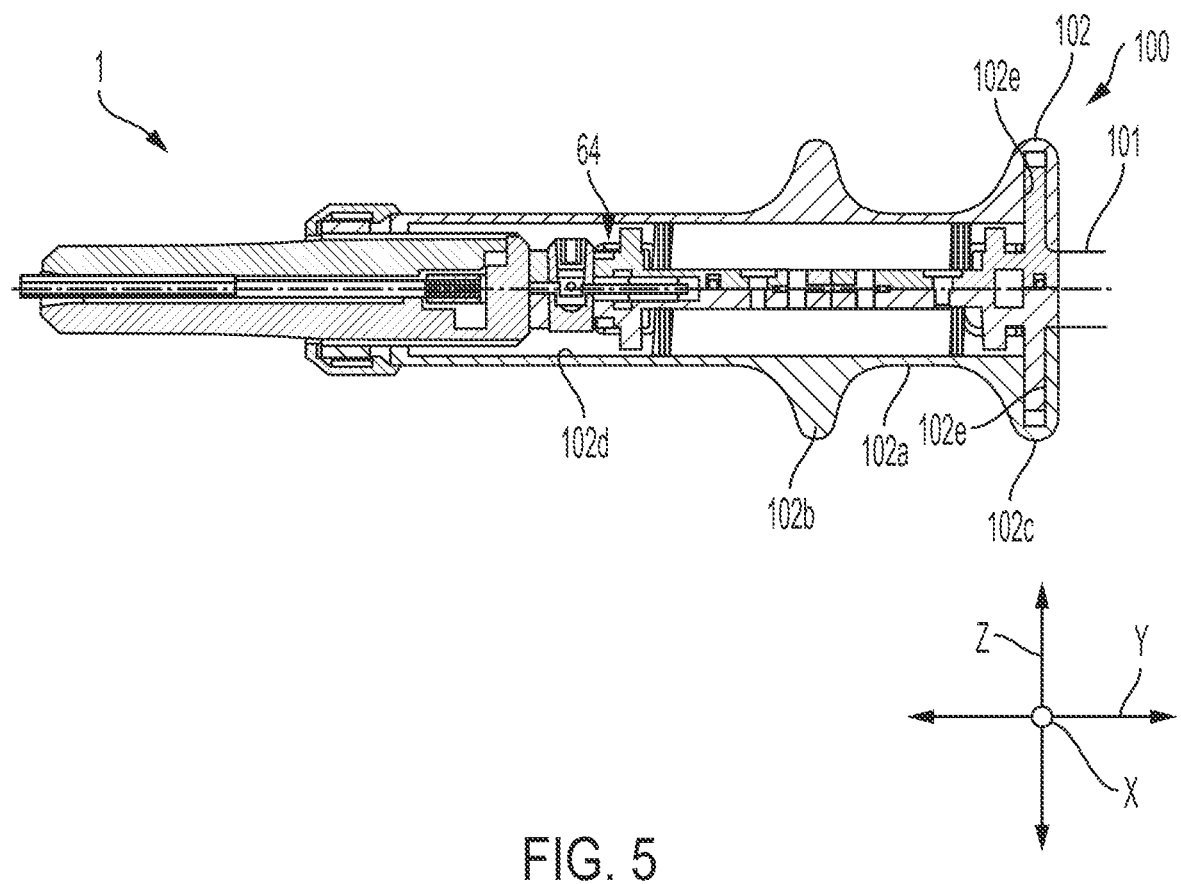
FIG. 5 is a top sectional view showing the proximal end of the endoscope treatment device in FIG. 1.

FIG. 3 is a sectional view showing the clip 10 of the endoscope treatment device 1. FIG. 4 is a sectional view showing a proximal end of the endoscope treatment device 1. FIG. 5 is a sectional view showing the proximal end of the endoscope treatment device 1. Hereinafter, configurations and operations will be described with reference to the schematic drawings and main portions will be described with reference to the detailed drawings.

(Configuration: Arm Portions 12 and 13 of the Clip 10)

As shown in FIGS. 1 and 2, the clip 10 includes a clip main body 11, a pressing tube 31, and a helical spring (elastic member) 36. The pressing tube 31 is formed in a cylindrical shape, but other tube shapes can be used, including those having cross-sections in the shape of an oval or in the shape of a polygon having n-sides, where n can be equal to or greater than 4. The pressing tube 31 has an interior volume and at least one open end to accommodate the insertion of the proximal end of the clip main body 11. The helical spring 36 is accommodated inside the pressing tube 31. The members forming the clip 10 in addition to the clip main body 11 are formed, for example, of a material such as a cobalt-chromium alloy, titanium, or stainless steel. The clip 10 is configured to be capable of being observed by MRI (Magnetic Resonance Imaging) radioscopy.

The clip main body 11 includes a first arm portion 12, a second arm portion 13, and a middle portion 14. The first arm portion 12 and the second arm portion 13 are disposed to extend from the proximal end side to the distal end side of the clip main body 11 and face each other. The middle portion 14 is disposed to be located between a proximal end of the first arm portion 12 and a proximal end of the second arm portion 13, and serves as a connection portion to connect the first arm portion 12 to the second arm portion 13. Moreover, the clip main body is configured to slidably move between a retracted position, e.g., toward the proximal end of the pressing tube 31, in which the arm portions 12 and 13 are within the interior volume of the pressing tube 31 and a deployed position, e.g., toward the distal end of the pressing tube 31, in which the arm portions 12 and 13 protrude from the open end of the pressing tube 31.

The first arm portion 12 and the second arm portion 13 are formed to be mutually separated in a natural state from the proximal end side to the distal end side. A claw 12a extending toward a side of the second arm portion 13 is formed at a distal end of the first arm portion 12. A claw 13a extending toward a side of the first arm portion 12 is formed at a distal end of the second arm portion 13.

Figure 6:
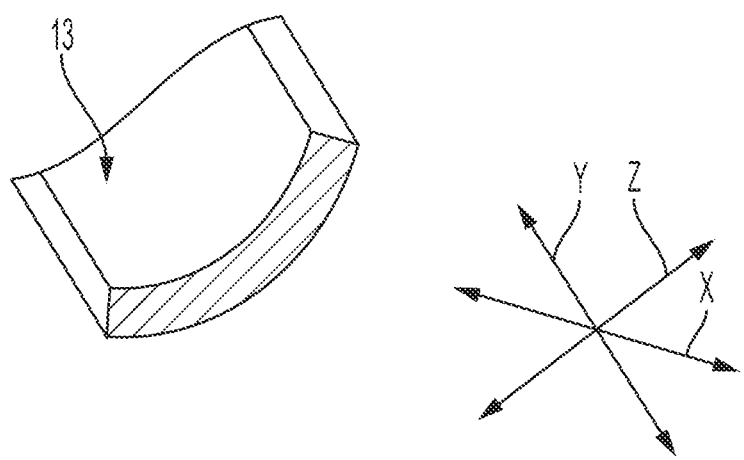
FIG. 6 a schematic perspective view taken along the cutting line A1-A1 in FIG. 3.

FIG. 6 is a schematic perspective view taken along the cutting line A1-A1 in FIG. 3. As shown in FIG. 6, in the second arm portion 13, a cross-sectional shape orthogonal to a longitudinal direction on the distal end side thereof is formed as an arc-like round shape. More specifically, a middle portion of the outside surface of the arm portion 13 in an orthogonal direction Z to be described below is formed in a curved shape that is convex toward the outside. A similar shape is present for arm portion 12.

Thus, for the first arm portion 12 and the second arm portion 13, the strength against bending is improved and frictional resistance to a sheath tube 50 to be described below is reduced, so that advancement and retraction operations can smoothly be performed.

(Configuration: First Locked Portions 16 and 17 of Clip 10)

Here, as shown in FIG. 1, an axis X in which the first arm portion 12 and the second arm portion 13 face each other, an axis Y parallel to an axial line C1 of the pressing tube 31, and an axis Z orthogonal to each of the axis X and the axis Y are defined. As shown in FIG. 2, two first locked portions 16 and 17 are provided at the proximal end of the first arm portion 12. The first locked portions 16 and 17 are provided to protrude from a lateral surface of the first arm portion 12 in the axis Z on a criterion plane S1 parallel to the axial line (central axial line) C1 of the pressing tube 31. The first locked portions 16 and 17 protrude in opposite directions.

FIG. 2 is a diagram of the endoscope treatment device in FIG. 1 when viewed in a direction orthogonal to the criterion plane S1. As shown in FIG. 2, the first locked portions 16 and 17 are formed to be line-symmetric with respect to the axial line C1.

As shown in FIG. 2, a proximal end surface 16a of the first locked portion 16 is formed to be separated and inclined from the first arm portion 12 (central axial line C1) toward the distal end side of the first locked portion 16. A distal end surface 16b of the first locked portion 16 is orthogonal to the axis Y. A proximal end surface 17a and a distal end surface 17b of the first locked portion 17 are formed to be line-symmetric to the proximal end surface 16a and the distal end surface 16b of the first locked portion 16 with respect to the axial line C1, respectively.

(Configuration: Protrusion Portions 18 and 19 of Clip 10)

As shown in FIGS. 1 and 2, two protrusion portions 18 and 19 are provided more distal than the first locked portions 16 and 17 in the first arm portion 12. The protrusion portions 18 and 19 protrude from the lateral surface of the first arm portion 12 in the axis Z. The protrusion portions 18 and 19 are formed to be line-symmetric with respect to the axial line C1. Lengths of the protrusion portions 18 and 19 protruding from the first arm portion 12 in the axis Z are longer than the first locked portions 16 and 17 which protrude from the first arm portion 12 in the axis Z.

(Configuration: Arm Portion 13 of Clip 10)

As shown in FIG. 1, the claw 13a extending toward the side of the first arm portion 12 is formed at the distal end of the second arm portion 13. In the second arm portion 13, second locked portions 21, 22 and protrusion portions 23, 24 are formed like the first locked portions 16, 17 and the protrusion portions 18, 19 of the first arm portion 12, respectively (the second locked portion 22 is referred to in FIG. 7 and the protrusion portion 24 is not shown). That is, the second locked portions 21 and 22 protrude from the lateral surface of the second arm portion 13 in the axis Z. The protrusion portions 23 and 24 are provided to protrude from the lateral surface of the second arm portion 13 in the axis Z more distal than the second locked portions 21 and 22 in the second arm portion 13. The second locked portions 21, 22 and the protrusion portions 23, 24 are disposed to be parallel to the first locked portions 16, 17 and the protrusion portions 18, 19 in the axis Z, respectively. That is, in FIG. 2, the first locked portions 16 and 17 overlap the second locked portions 21 and 22 and the protrusion portions 18 and 19 overlap the protrusion portions 23 and 24.

In a side view shown in FIG. 1, the first arm portion 12 and the second arm portion 13 are formed at positions which are line-symmetric with respect to the axial line C1.

For the clip main body 11, a plate formed for example, of a cobalt-chromium alloy or the like is punched in a shape in which the arm portions 12 and 13, the middle portion 14, the first locked portions 16 and 17, the second locked portions 21 and 22, and the protrusion portions 18, 19, 23, and 24 are spread in a planar form. Then, the punched member is integrally formed in a C shape in a side view by bending a connection portion of the first arm portion 12 and the middle portion 14 and a connection portion of the second arm portion 13 and the middle portion 14.

(Configuration: Connection Member 63)

Figure 9A:
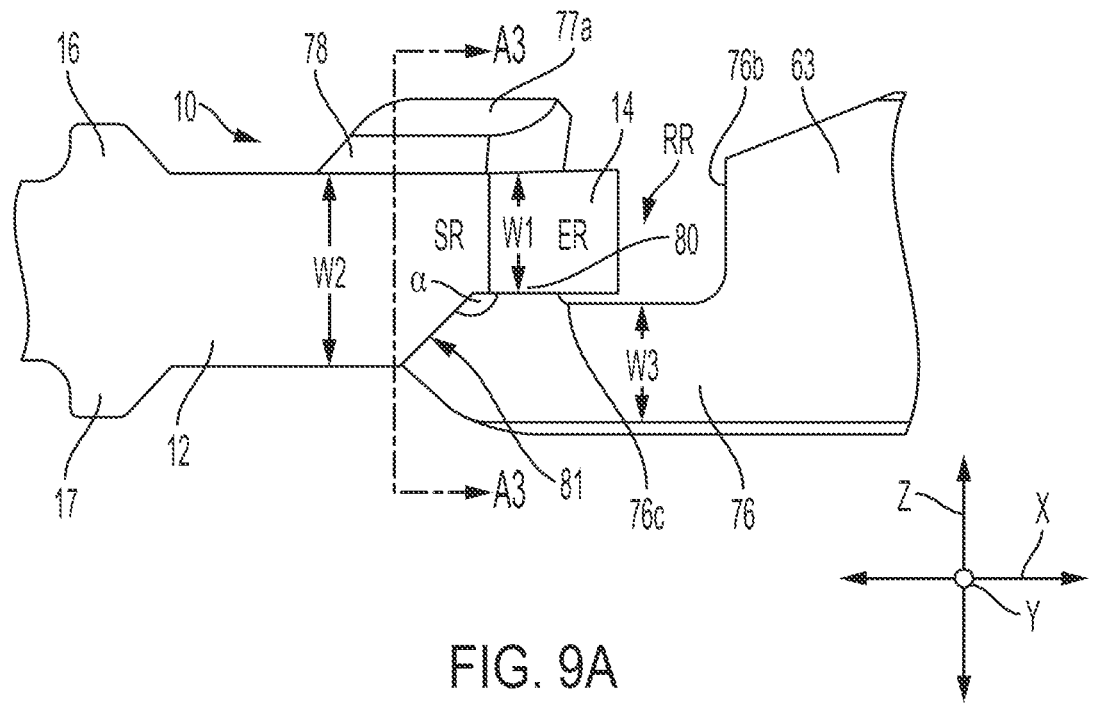
FIG. 9A is an enlarged side view illustrating an exemplary configuration of an embodiment of engagement mechanism between a clip and a connection member.

The connection member 63 includes a hooking structure 77 at the distal end of a bridge 76, and a through hole 76a is formed at the proximal end of the bridge 76. A surface 76b (see FIG. 2) is formed facing an hook surface of the hooking structure 77. The surface 76b may also be an inclination surface as shown in FIG. 2 with respect to the axial line C1, or as shown in FIG. 9A, may be a surface extending upwardly in a direction orthogonal to the axial line C1.

When a turned portion of a wire 73a of a loop portion 73 is inserted into the through hole 76a, the connection member 63 is connected to the loop portion 73 to be rotatable about an axis parallel to the axis X (rotatable in an arrow direction D in FIG. 2).

The width of the connection member 63 is the outer diameter of the bridge 76 in a direction orthogonal to the central axial line C1 when the hooking structure 77 is disposed on the distal end side of the bridge 76. The width of the connection member 63 is slightly less than the inner diameter of a helical spring 36, the inner diameter of a coil sheath 66, and the inner diameter of a distal end member 67.

By disposing the middle portion 14 between the hooking structure 77 of the connection member 63 and the surface 76b of the connection member 63, the hooking structure 77 can engage with the middle portion 14.

(Configuration: Engagement Portion Between Clip 10 and Connection Member 63)

First Embodiment

Figure 9B:
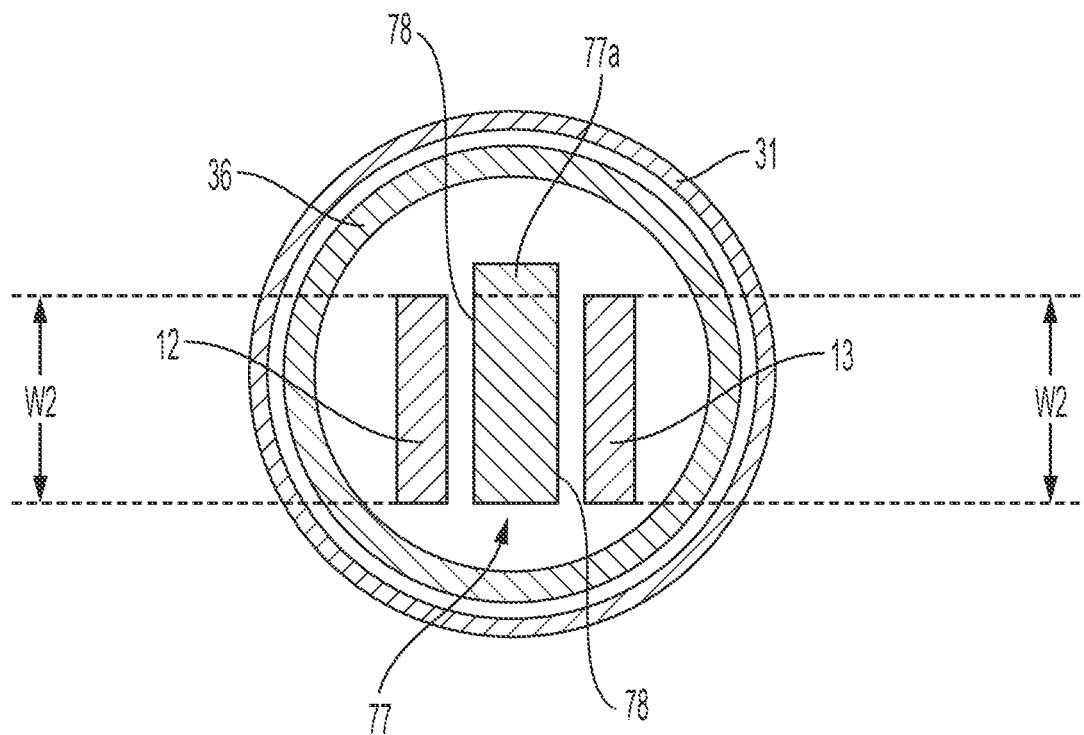
FIG. 9B is a schematically, representational cross-sectional view taken from line A3-A3 of FIG. 9A.

FIG. 9A is an enlarged side view illustrating an exemplary configuration of an engagement mechanism between the clip 10 and a connection member 63, and FIG. 9B is a cross-sectional view taken from line A3-A3 of FIG. 9A. As shown in FIG. 9A, the engagement mechanism includes the hooking structure 77 and an engaging portion 15 (also referred to as a stepped connector). The stepped connector 15 includes an engaging region ER configured to engage with a hook surface 79 (see FIG. 10B) of the hooking structure 77 and two side regions SR arranged adjacent to two lateral surfaces 78 of the hooking structure 77 (see FIG. 9B). The two lateral surfaces 78 and the hook surface 79 are located on a distal end portion of the hooking structure 77, and the bridge 76 includes a first end connected to the distal end portion of the hooking structure 77 and extending therefore to form part of a recess RR of the connection member 63. The engaging region ER is on the middle portion 14 of the clip 10, and the two side regions SR are on the proximal ends of the arm portion 12 and the arm portion 13 of the clip 10.

The engaging region ER has a width W1 extending in the axis Z and in a direction orthogonal to the axial line C1 in FIG. 2, the two side regions SR of the arm portions 12 and 13 each have a width W2 also extending in the axis Z and in a direction orthogonal to the axial line C1 in FIG. 2, and a bridge 76 of the connection member 63 has a width W3 also extending in the axis Z and in a direction orthogonal to the axial line C1 in FIG. 2. The relationships among the widths W1, W2 and W3 may be set such that the width W2 is greater than the width W1, and preferably, 1.5 times or up to 2 times greater than the width W1. The width W1 may be set to be substantially the same as the width W3. Moreover, the two side regions SR may have a first width on the arm portion 12 side and a second width on the arm portion 13 side, and the first width is different from the second width, i.e. have different lengths. However, the width W1 is smaller than either the first width or the second width of the two side regions SR. In other words, each of the first width and the second width is greater than the width W1 and preferably is 1.5 times to 2 times greater than the width W1.

The stepped portion 15 also includes a first seating surface 80 and a second seating surface 81. The first seating surface 80 may be part of a bottom surface of the middle portion 14, and the second seating surface 81 may be part of a proximal end surface of the arm portion 12. The stepped portion 15 has an angle α that is formed by the first seating surface 80 and the second seating surface 81. The angle α may be a right angle (90 degrees) or an obtuse angle (greater than 90 degrees to 180 degrees). The first seating surface 80 may seat on (or be in contact with) an upper surface 76c of the bridge 76.

While not shown, a stepped portion that is formed by the arm portion 13 and the middle portion 14 may have the same configuration as the stepped portion 15. The stepped portion also includes one region where the middle portion 14 contacts the hooking structure 77 and the other region where the arm portion 13 is adjacent to the hooking structure 77. The two regions may have the same configuration as the engaging region ER and the two side regions SR, respectively. The stepped portion may also include two seating surfaces that may have the same configuration as the first and second seating surfaces S1 and S2. One of the two seating surfaces may be part of a proximal end surface of the arm portion 13, and the other seating surface may be part of a bottom surface of the middle portion 14. The not-shown stepped portion may also have the same angle α that is formed by the two seating surfaces, one of which may be in contact with the upper surface 76c of the bridge 76.

Figure 13:
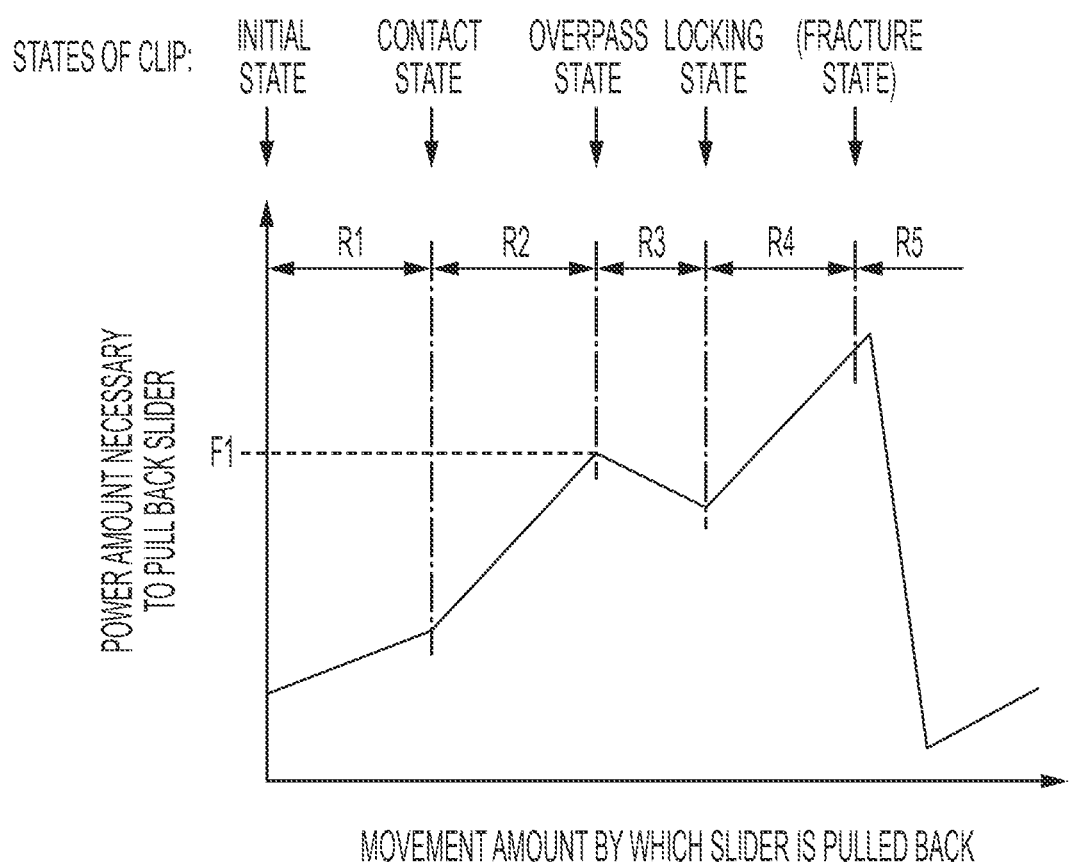
FIG. 13 is a schematic diagram showing an amount of power necessary to pull back a slider with respect to a movement amount by which the slider is pulled back in the endoscope treatment device in FIG. 1.

As shown in FIG. 13, which will be described in detail later, when the clip 10 is strongly pulled back toward the proximal end by the hooking structure 77, the bridge 76, which is connected to and supports the hooking portion, has to bear a strong pulling force coming from the manipulation portion 100. If the width W3 of the bridge 76 is too narrow with respect to the width W1 of the region R1, the strength of the connection member 63 in its axis direction becomes weak, thereby causing deformation of the hooking structure 77. As a result, the arm portions 12 and 13 of the clip 10 may come off the hooking structure 77 due to the deformation before the claws 12a and 13a of the clip 10 successfully grasp a target tissue. By increasing the width W3 to be substantially the same as the width W1, the strength of the bridge 76 can be increased in the axis direction. Thus, when the clip 10 is pulled back toward the proximal end by the hooking structure 77, the clip 10 can be prevented from coming off the connection member 63 before the completion of the grasping operation.

On the other hand, the clip 10 may be rotatable inside the pressing tube 31 by rotating the hooking structure 77 around the axis direction of the connection member 63. In order to prevent the arm portions 12 and 13 from coming off the hooking structure 77 inside the pressing tube 31 when the hooking structure 77 is rotated, it is necessary to strengthen the connection structure between the clip 10 and the connection member 63 in the rotation direction. In this exemplary embodiment, the region R2 between the arm portions 12 and 13 and the hooking structure 77 is larger than the contact region R1 by setting the width W2 to be greater than the width W1 and preferably to be 1.5 times to 2 times greater than the width W1. As shown in FIG. 9B, the arm portions 12 and 13 overlap with the entire sides 78 of the hooking structure 77 in a side view seen from the axis Y except for a top 77a of the hooking structure 77. With this exemplary configuration, the strength of the connection structure in the rotation direction can be increased by providing more available contact area. Thus, the clip 10 can be prevented from coming off the connection member 63 when the connection member 63 is rotated before the completion of the grasping operation.

Second Embodiment

Figure 10A:
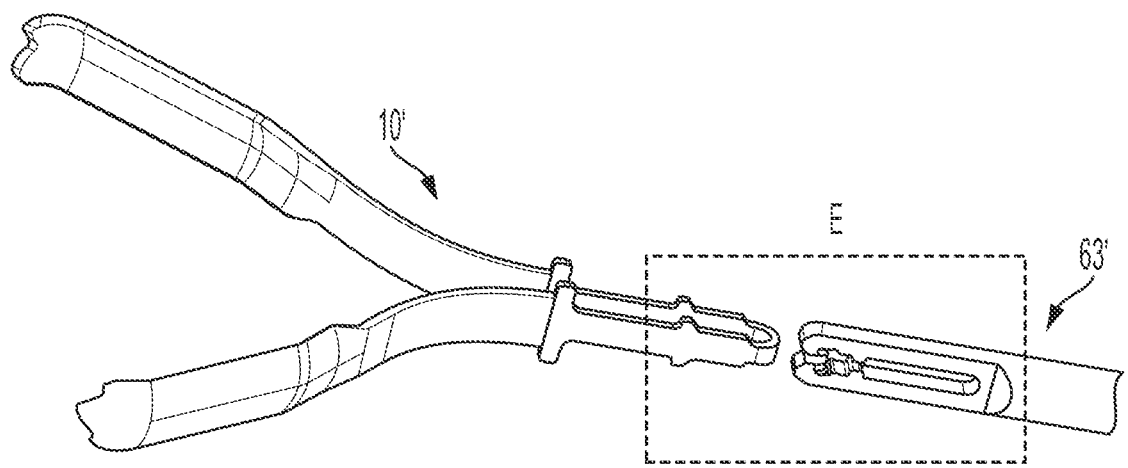
FIG. 10A is a perspective view schematically illustrating an exemplary configuration of another embodiment of an engagement mechanism between a clip and a connection member.
Figure 10B:
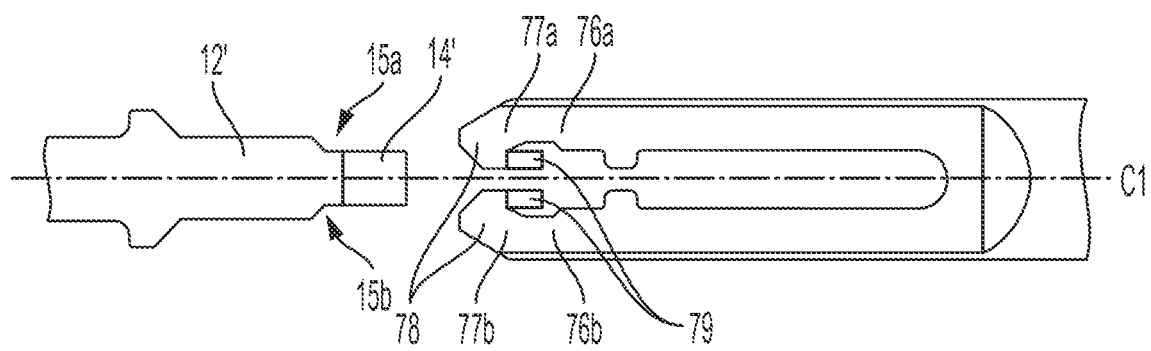
FIG. 10B is an enlarged view of region E in FIG. 10A.

FIG. 10A is a perspective view schematically illustrating a clip 10' and a connection member 63' according to a second exemplary embodiment, and FIG. 10B is an enlarged view of region E in FIG. 10A. As shown in FIGS. 10A and 10B, different from the first exemplary embodiment, the engagement mechanism of the second exemplary embodiment includes first and second hooking structures 77a and 77b and first and second stepped connectors 15a and 15b. In this exemplary embodiment, each of the first and second hooking structures 77a and 77b may be the same as the hooking structure 77 described in the first embodiment. That is, the first hooking structure 77a includes the two lateral surfaces 78 connected by the hook surface 79, and the second hooking structure 15b includes the two lateral surfaces 78 connected by the hook surface 79. Also, each of the first and second stepped connectors 15a and 15b may be the same as the stepped connector 15 described in the first embodiment. That is, the first stepped connector 15a includes an engaging region ER and two side regions SR, and the second stepped connector 15b includes an engaging region ER and two side regions SR. Thus, the engaging region of the first stepped connector engages with the hook surface of the first hooking structure, and each of the two side regions of the first stepped connector are adjacent to a respective one of the two lateral surfaces of the first hooking structure. The engaging region of the second stepped connector engages with the hook surface of the second hooking structure, and each of the two side regions of the second stepped connector are adjacent to a respective one of the two lateral surfaces of the second hooking structure. However, the first and second hooking structures 77a and 77b may have different configurations from each other, and the first and second stepped connectors 15a and 15b may also have different configurations from each other.

Also, in the engagement mechanism of the second exemplary embodiment, the first and second stepped connectors 15a and 15b are formed at the proximal end of each of the arm portions 12' and 13', and the first and second hooking structures 77a and 77b are formed at the distal end of the connection member 63'. The first and second stepped connector 15a and 15b are configured to be line-symmetric along the axial line C1 in a side view, the first and second hooking structures 77a and 77b are configured to be line-symmetric along the axial line C1 in the side view, and two corresponding bridges 76a and 76b are configured to be line-symmetric along the axial line C1 in the side view.

In this exemplary embodiment, the width relationships among the first and second stepped connectors 15a and 15b and the bridges 76a and 76b are also the same as those described in the first exemplary embodiment.

Figure 10C:
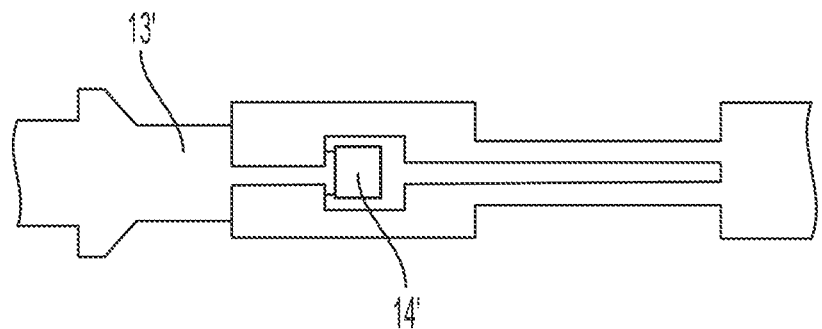
FIG. 10C is a schematic, representational cross-sectional view illustrating the engagement mechanism of the clip and the connection member of FIG. 10A.
Figure 10D:
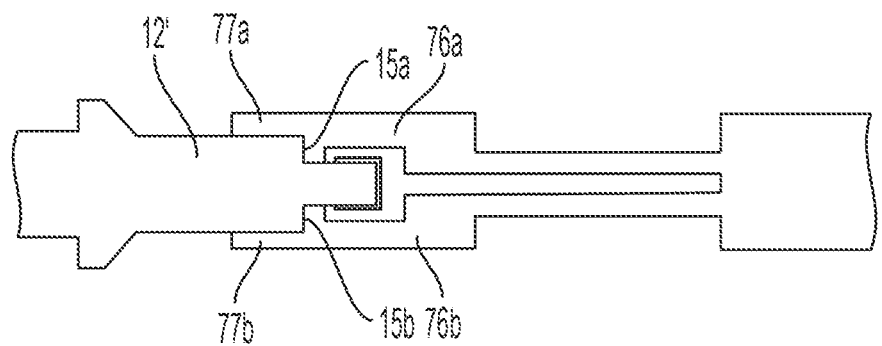
FIG. 10D is a schematic, representational side view illustrating the engagement mechanism.

FIG. 10C is a cross-sectional view schematically illustrating the engagement mechanism of the clip 10' and the connection member 63', and FIG. 10D is another schematic, representational cross-sectional view illustrating the engagement mechanism of the clip 10' and the connection member 63'. Compared to the first exemplary embodiment, the second exemplary embodiment using a configuration of double-stepped connectors and double-hooking structures, which can provide a more stable engagement between the clip 10' and the connection member 63'.

Third Embodiment

Figure 11A:
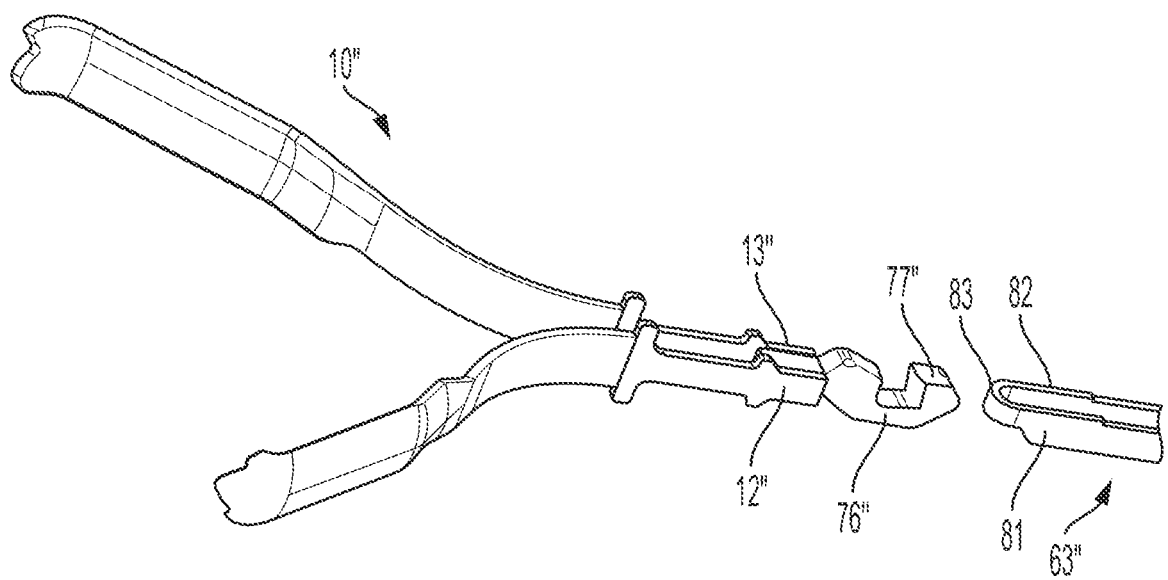
FIG. 11A is a perspective view schematically illustrating a clip and a connection member according to another embodiment.
Figure 11B:
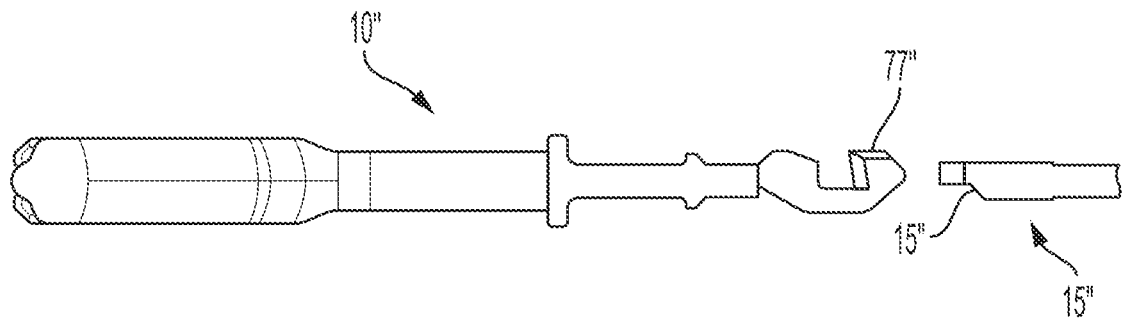
FIG. 11B is a side view of FIG. 11A.

FIG. 11A is a perspective view schematically illustrating a clip 10" and a connection member 63" according to a third exemplary embodiment, and FIG. 11B is a schematic, representational cross-sectional view of FIG. 11A. As shown in FIGS. 11A and 11B, different from the first exemplary embodiment, the engagement mechanism in the third exemplary embodiment is configured to have a hooking structure 77" extended from the arm portions 12" and 13" (or integrally formed with the arm portions 12" and 13"), and the connection member 64" that is hooked on the hooking structure 77". The connection member 64" is configured to have a stepped connector 15" formed by two arm portions 81 and 82 and a middle portion 83. The middle portion 83 is also referred to as a connection portion that connects the arm portion 81 to the arm portion 82. Thus, in the third exemplary embodiment, the connection member 64" having the stepped connector 15" is hooked on the hooking structure 77" that is attached to the clip 10".

The hooking structure 77" may be attached to the clip 10" by welding or the like.

Figure 11C:
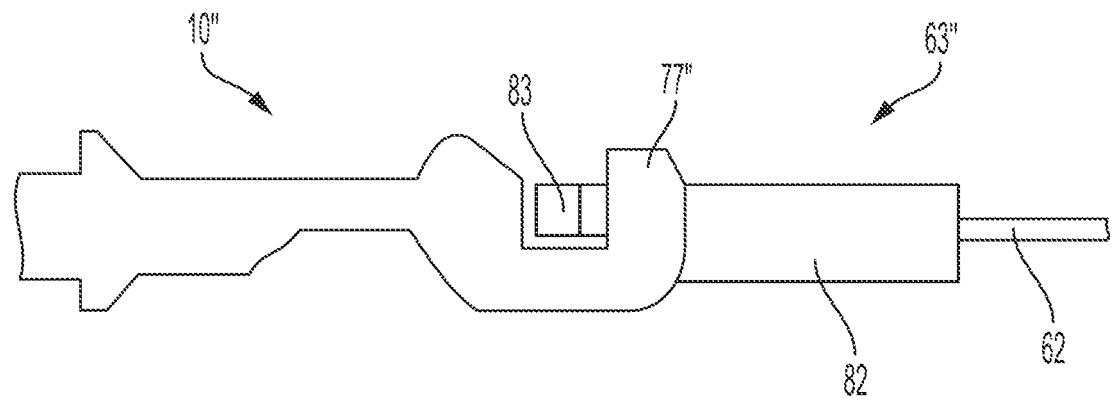
FIG. 11C is a schematic, representational cross-sectional view illustrating the engagement mechanism of the clip and the connection member of FIG. 11A.
Figure 11D:
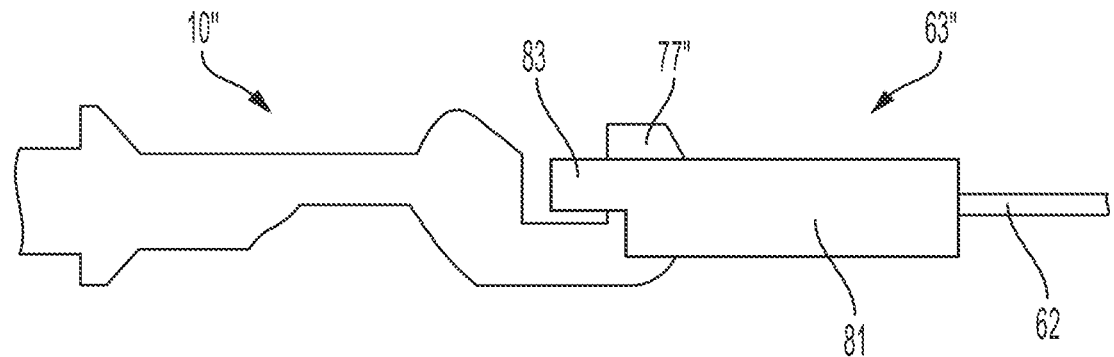
FIG. 11D is a schematic, representational side view schematically illustrating the engagement mechanism.

FIG. 11C is a cross-sectional view schematically illustrating the engagement mechanism between the clip 10" and the connection member 63", and FIG. 11D is another schematic, representational cross-sectional view illustrating the engagement between the clip 10" and the connection member 63". Different from the first exemplary embodiment, in the third exemplary embodiment, the hooking structure 77" is part of the clip 10" and is formed on the distal end (connection portion 14") of the clip 10", and the stepped connector 15" is part of the connection member 63" and located at the distal end of the connection member 63". The proximal end of the connector member 63" is connected to a linear member 74 (in FIG. 1).

(Configuration: Locking Portion 32 of Clip 10)

Figure 7:
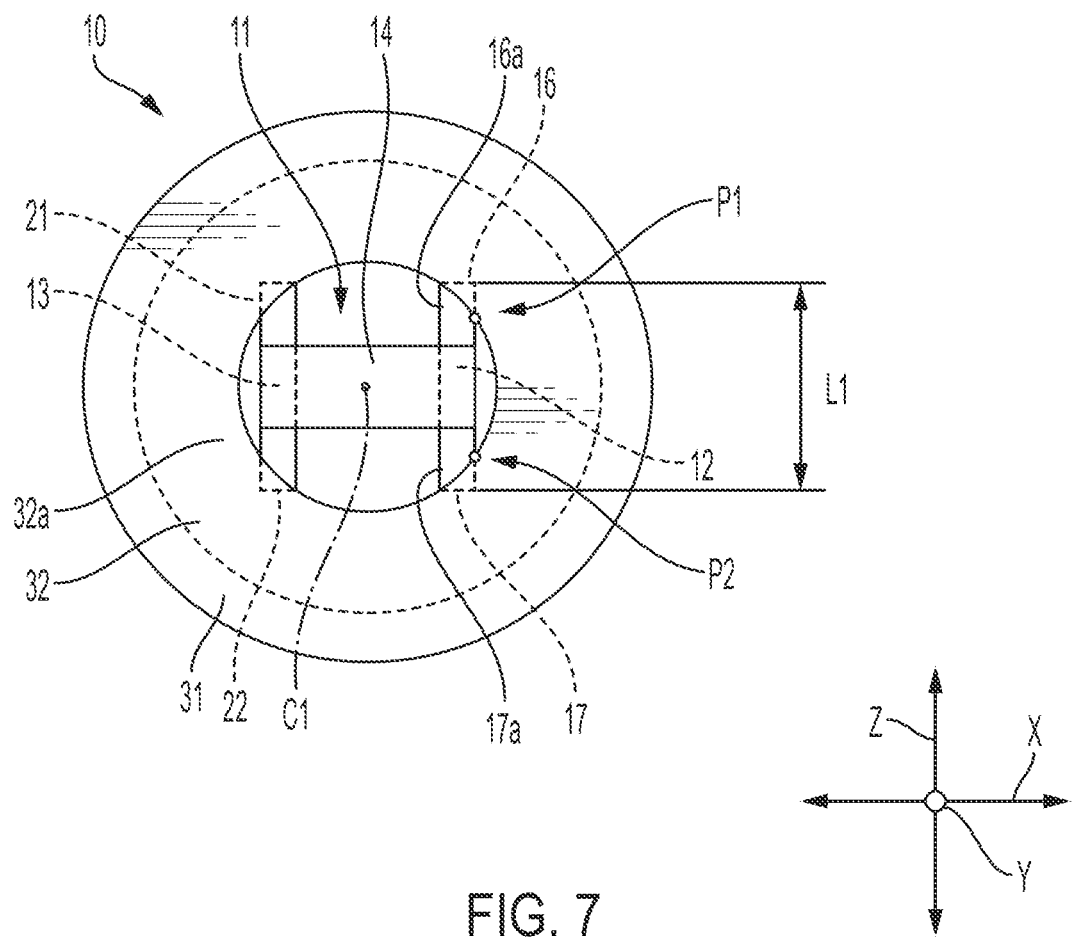
FIG. 7 is a diagram schematically showing a state of the clip unit in FIG. 1 when viewed from the proximal end side.

As shown in FIGS. 2 and 7, on the inner circumferential surface of the proximal end of the pressing tube 31, a locking portion 32 protrudes over the entire inner circumference surface. When viewed in the direction of axis Y shown in FIG. 7, an edge 32a of the locking portion 32 on a side of the axial line C1 is formed in a circular shape that is coaxial with the pressing tube 31. As shown in FIG. 2, a proximal end surface 32b (proximal-end-side end surface) and a distal end surface 32c (distal-end-side end surface) of the locking portion 32 are orthogonal to the axis Y.

Portions on the proximal end side of the protrusion portions 18 and 19 in the first arm portion 12, portions on the proximal end side of the protrusion portions 23 and 24 in the second arm portion 13, and the middle portion 14 can be inserted into the locking portion 32. As shown in FIG. 7, a length L1 between an end of the first locked portion 16 and an end of the first locked portion 17 in the axis Z is less than the inner diameter of the locking portion 32. In an initial state to be described below, parts of the first locked portions 16 and 17 are set to overlap the locking portion 32 when viewed along the axis Y. That is, in the state shown in FIG. 7, the edge 32a is set such that the length L1 of the first locked portions 16 and 17 is longer than a height (a length of a line segment between positions P1 and P2 in FIG. 7) of the edge 32a in which the first locked portions 16 and 17 face each other at the positions P1 and P2.

As shown in FIG. 2, a tapered surface 31a is formed over the entire inner circumference surface at the distal end of the pressing tube 31. The diameter of the tapered surface 31a expands toward the distal end side of the pressing tube.

The pressing tube 31 and the locking portion 32 are integrally formed of a material such as, for example, a 64 titanium alloy (Ti-6AL-4V) or a cobalt-chromium alloy.

(Configuration: Helical Spring 36 of Clip 10)

As shown in FIG. 3, an end turn portion 36b is provided at the distal end of the helical spring 36. The inner diameter of the formed end turn portion 36b is less than that of the other portions of the helical spring 36.

When the helical spring 36 is accommodated inside the pressing tube 31, the distal end thereof interlocks with the protrusion portions 18, 19, 23, and 24 and the proximal end thereof interlocks with the locking portion 32. The proximal end of the helical spring 36 and the locking portion 32 may be fixed by welding or the like.

The portions on the proximal end side of the protrusion portions 18 and 19 in the first arm portion 12, the portions on the proximal end side of the protrusion portions 23 and 24 in the second arm portion 13, and the middle portion 14 can be inserted into the helical spring 36. When the protrusion portions 18, 19, 23, and 24 are moved toward the proximal end side, the protrusion portions 18, 19, 23, and 24 interlock with the end turn portion 36b of the helical spring 36. Even when the helical spring 36 does not include the end turn portion 36b, the same advantage can be obtained by using a separate member such as a washer at the distal end of the helical spring 36.

In the initial state of the clip 10 shown in FIGS. 1 and 2, the proximal end of the first arm portion 12, the proximal end of the second arm portion 13, and the middle portion 14 are located at the distal end side with respect to the locking portion 32 inside the pressing tube 31. The first locked portions 16 and 17 and the second locked portions 21 and 22 do not come into contact with the locking portion 32 of the pressing tube 31. Wires 36a of the helical spring 36 adjacent to each other in the axis Y are separated from each other. The helical spring 36 is compressed in the axis Y slightly more than in the natural state. The distal end of the first arm portion 12 and the distal end of the second arm portion 13 of the clip main body 11 are separated from each other so as to be in an opened state.

(Configuration: Relation Between Clip Main Body 11 of Clip 10 and Pressing Tube 31)

In the clip 10 with the above-described configuration, the first arm portion 12 and the second arm portion 13 are separated in the axis X in the initial state. Therefore, as shown in FIG. 7, when the first locked portion 16 is viewed from the proximal end side, the first locked portion 16 is overlapped by a portion of the edge 32a at the position P1 of the locking portion 32. That is, when first arm portion 12 is moved toward the proximal end side with respect to the pressing tube 31, the first locked portion 16 comes into contact with the portion of the edge 32a at the position P1. The portion of the edge 32a at the position P1 comes into point contact with the first locked portion 16.

Likewise, when the first arm portion 12 is moved toward the proximal end side with respect to the pressing tube 31, the first locked portion 17 comes into contact with the portion of the edge 32a at the position P2. A part of the edge 32a at the position P2 comes into point contact with the first locked portion 17. A proximal end surface 16a of the first locked portion 16 comes into contact with the portion of the edge 32a at the position P1. A proximal end surface 17a of the first locked portion 17 comes into contact with the portion thereof at the position P2.

Positions of the edge 32a corresponding to the positions P1 and P2 are indicated by positions Q1 and Q2 in FIG. 2.

When the second arm portion 13 integrally formed with the first arm portion 12 is moved toward the proximal end side with respect to the pressing tube 31, the second locked portions 21 and 22 come into contact with the locking portion 32 of the pressing tube 31, like the first locked portions 16 and 17 of the first arm portion 12.

(Configuration: Treatment Device Body 40)

Next, the configuration of the treatment device body 40 will be described.

As shown in FIGS. 1 and 2, the treatment device body 40 includes the sheath tube 50, an insertion portion 60 and a manipulation portion 100. The insertion portion 60 is inserted inside the sheath tube 50 to be advanceable and retractable. The manipulation portion 100 is attached to the proximal end of the insertion portion 60.

The sheath tube 50 can be formed of, for example, a fluorine resin such as polytetrafluoroethylene (PTFE) or a resin material such as high-density polyethylene (HDPE).

(Configuration: Sheath Portion 61 of Treatment Device Body 40)

The insertion portion 60 includes a sheath portion 61 and a manipulation wire 62. The manipulation wire 62 is inserted into the sheath portion 61 so as to be advanceable and retractable. The connection member 63 is connected to the distal end of the manipulation wire 62. The connection member 63 is provided to be rotatable about an axis parallel to the axis X with respect to the manipulation wire 62.

The sheath portion 61 includes a coil sheath 66 and a distal end member (stopper portion) 67 fixed to the distal end of the coil sheath 66. The coil sheath 66 is formed, for example, of stainless steel with a high compression resistance such as SUS301 of JIS (Japanese Industrial Standards).

A coil formed by densely winding a wire (not shown) in the axis Y can be used as the coil sheath 66. The coil sheath 66 has flexibility and is strong against a compressive force in the axis Y. The inner diameter of the coil sheath 66 is almost the same as the inner diameter of the helical spring 36.

The distal end member 67 is formed of, for example, stainless steel in a cylindrical shape. The inner diameter of the distal end member 67 is less than the inner diameter of the coil sheath 66. The outer diameter of the distal end member 67 is greater than that of the coil sheath 66 or the pressing tube 31. A concave portion 67a is formed on the outer circumferential surface of the proximal end of the distal end member 67 by reducing the outer diameter thereof. When the distal end of the coil sheath 66 engages with the concave portion 67a, the distal end member 67 and the coil sheath 66 are fixed together by laser welding or the like.

Thus, on the inner circumferential surface of the distal end of the sheath portion 61, a stepped portion 68 is formed in a connection portion of the coil sheath 66 and the distal end member 67 by reducing the inner diameter of the distal end member 67 provided more distal than the coil sheath 66 with respect to the coil sheath 66. The inner diameter of the distal end member 67 is formed so that the distal end member 67 does not engage with the first locked portions 16 and 17 and the second locked portions 21 and 22 when the clip 10 engages with the locking portion 32, as will be described below.

(Configuration: Distal End Member 67 of Treatment Device Body 40)

A concave portion is formed over the entire inner circumferential surface of the distal end of the distal end member 67 and a support member 69 is disposed more distal than the concave portion. In this example, the support member 69 is formed in a cylindrical shape. The support member 69 has an inner diameter that is slightly greater than the outer diameter of the pressing tube 31 and has dimensions such that the proximal end of the pressing tube 31 can be accommodated therein. In the concave portion on the inner circumferential surface of the support member 69, a surface facing forward is a distal end support surface (distal end surface) 67b. The distal end support surface 67b can come into contact with the proximal end surface of the pressing tube 31. The clip 10 is disposed on the distal end side of the sheath portion 61. The support member 69 can support the outer circumferential surface of the pressing tube 31 coming into contact with the distal end support surface 67b.

In this configuration, shaking of the clip 10 with respect to the support member 69 can be suppressed to be as small as possible, and thus an inclination of the clip 10 with respect to the support member 69 can be allowed to some extent. Therefore, the endoscope treatment device 1 can be inserted smoothly even into the bending shape of an endoscope channel or the like.

(Configuration: Manipulation Wire 62 of Treatment Device Body 40)

The manipulation wire 62 is formed of, for example, a single line mode of metal or a twisted line made of a metal. A loop portion 73 is provided at the distal end of the manipulation wire 62 via a diameter expansion portion 72. A linear member 74 (see FIG. 1) is formed by the manipulation wire 62 and the loop portion 73.

The diameter expansion portion 72 is formed of, for example, a metal or the like in a cylindrical shape. The outer diameter of the diameter expansion portion 72 is less than the inner diameter of the coil sheath 66 and is greater than the inner diameter of the distal end member 67. When the distal end surface of the diameter expansion portion 72 comes into contact with the stepped portion 68, the protrusion amount of the loop portion 73 with respect to the sheath portion 61 is regulated up to a length L2 (see FIG. 22). The length L2 is the maximum protrusion amount of the loop portion 73 allowed by the distal end member 67.

The loop portion 73 is formed by turning back a wire 73a. The wire 73a is turned back so that the turned portion is on the distal end side of the wire 73a. Both ends of the wire 73a are fixed to the diameter expansion portion 72 by brazing, resistance welding, or the like.

(Configuration: Manipulation Portion 100 of Treatment Device Body 40)

As shown in FIG. 1, the manipulation portion 100 includes a manipulation portion main body 101, a slider 102, and a fracture mechanism 64. The manipulation portion main body 101 is installed on the proximal end of the coil sheath 66. The slider 102 is provided to be externally fitted to the manipulation portion main body 101 and to be slidable with respect to the manipulation portion main body 101 in the axis Y. The fracture mechanism 64 is connected to the proximal end of the manipulation wire 62 and the slider 102.

The manipulation portion main body 101 is formed in a rod shape extending in the axis Y. A finger hooking portion 101a is attached to the proximal end of the manipulation portion main body 101. On the proximal end side of the finger hooking portion 101a, a planar portion 101c is provided so that the manipulation portion 100 can be easily grasped with two hands (see FIG. 4). A slit 101b extending in the axis Y is formed in the manipulation portion main body 101.

Figure 8:
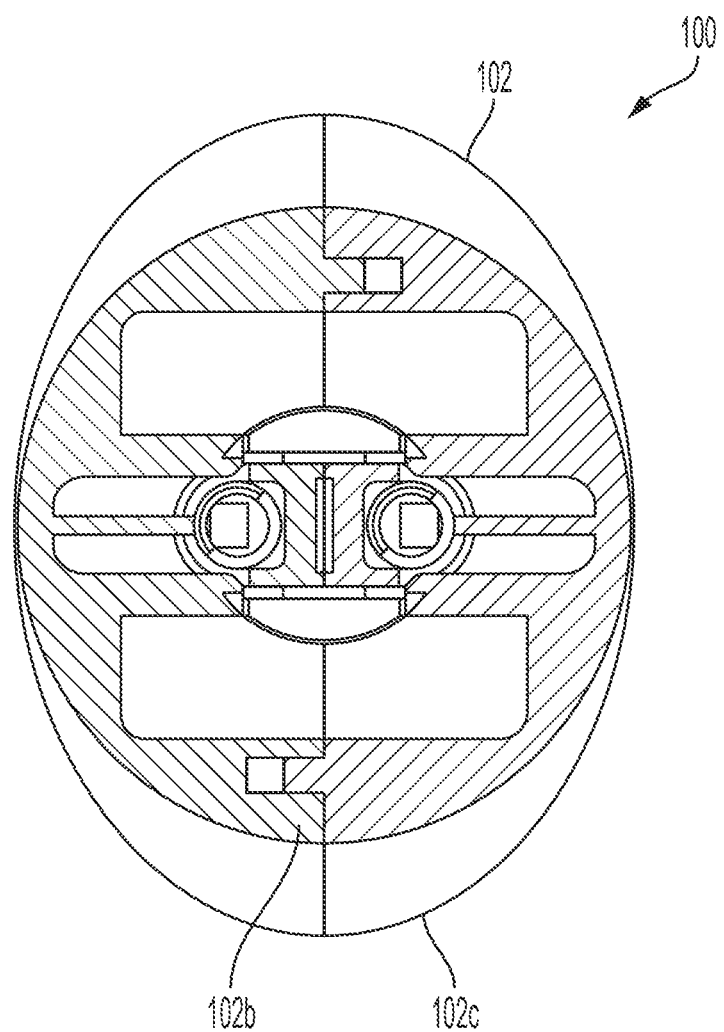
FIG. 8 is a diagram taken along the cutting line A2-A2 in FIG. 4

The slider 102 is formed in a cylindrical shape. On the outer circumferential surface of the slider 102, a concave portion 102a is formed around the circumference. A pair of flange portions 102b and 102c are formed in the slider 102 in the axis Y so that the concave portion 102a is located between a pair of flange portions 102b and 102c. The pair of flange portions 102b and 102c have elliptical shapes when viewed in the axis Y (see FIGS. 4 and 8). Thus, the slider 102 can be easily grasped. When the manipulation portion 100 of the endoscope treatment device 1 is packed, space can be saved. As shown in FIG. 5, a groove 102e extending in the axis Z is formed in a tube hole 102d of the slider 102.

When the slider 102 engages with the slit 101b of the manipulation portion main body 101, the movement range of the slider 102 with respect to the manipulation portion main body 101 in the axis Y is regulated. The fracture mechanism 64 is disposed inside the tube hole 102d of the slider 102, as shown in FIGS. 4 and 5. In other words, the fracture mechanism 64 is built in the manipulation portion 100.

(Operation of Treatment Device Body 40)

Next, an operation of the treatment device body 40 will be described.

In the above-described configuration, by sliding the slider 102 in the axis Y with respect to the manipulation portion main body 101, the manipulation wire 62 can be manipulated to be advanced and retracted in the axis Y, thereby advancing and retracting the clip 10 with respect to the pressing tube 31.

(Action: Initial State)

Next, a technique used to ligate a target tissue with the clip 10 of the endoscope treatment device 1 with the above-described configuration will be described.

Figure 12:
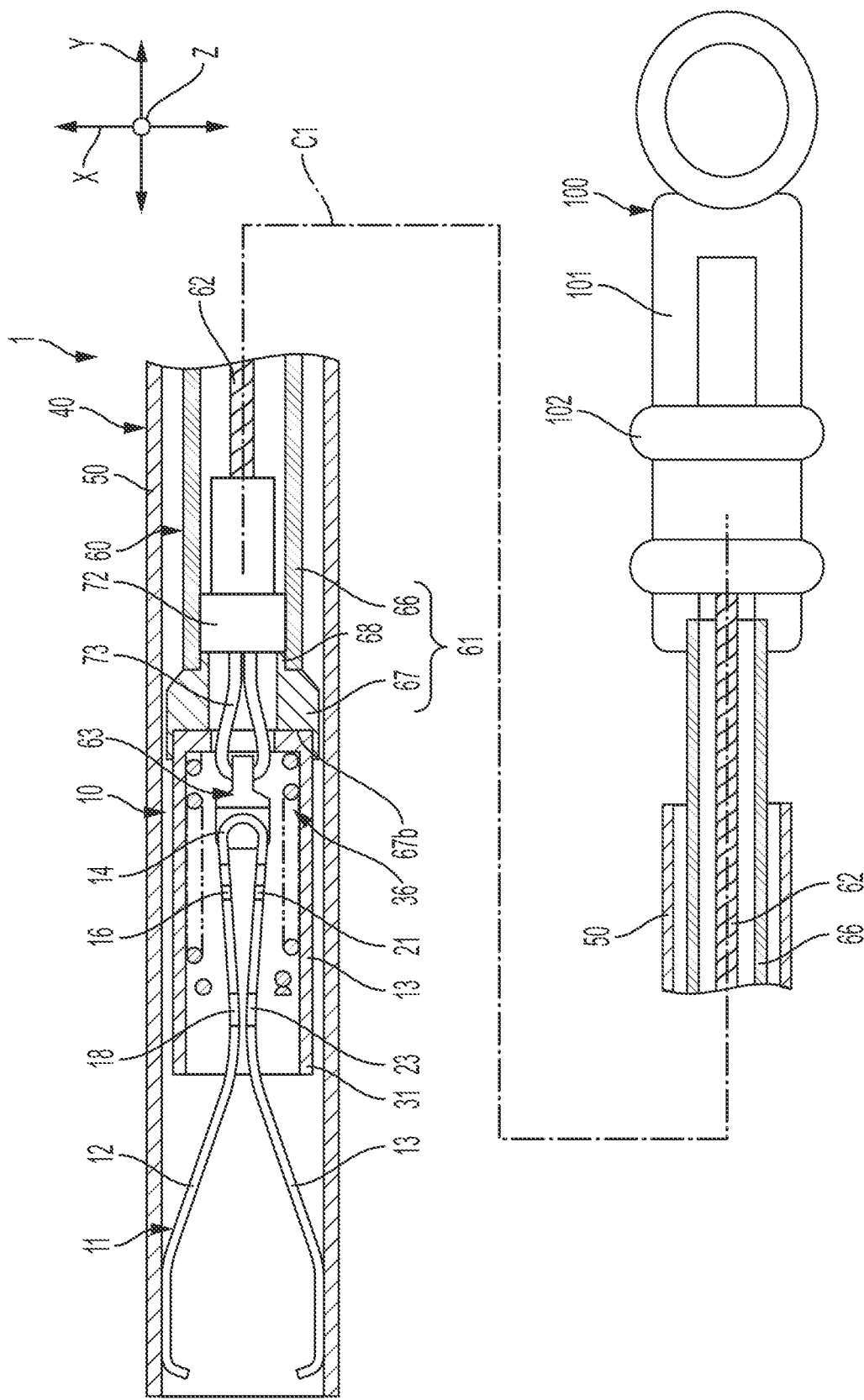
FIG. 12 is a schematic diagram showing an example usage of the endoscope treatment device in FIG. 1.

When the endoscope treatment device 1 is provided to a user who is an operator, as shown in FIG. 12, the sheath tube 50 is pushed to the insertion portion 60 so that the clip 10 installed in the treatment device body 40 is hidden. The helical spring 36 of the clip 10 in the initial state is compressed in the axis Y slightly more than in the natural state. Therefore, the proximal end surface of the pressing tube 31 comes into contact with the distal end support surface 67b. The distal end surface of the diameter expansion portion 72 comes into contact with the stepped portion 68 and the loop portion 73 protrudes up to the maximum protrusion amount from the distal end member 67.

When the endoscope treatment device 1 is used, an endoscope insertion portion of an endoscope (not shown) is inserted into the body of a patient. The sheath tube 50 of the endoscope treatment device 1 is inserted from the proximal end of a channel of the endoscope and the sheath tube 50 protrudes from the distal end of the channel of the endoscope. When the sheath tube 50 is pulled back with respect to the insertion portion 60, the clip 10 protrudes from the distal end side of the sheath tube 50, as shown in FIG. 1. Thus, the arm portions 12 and 13 of the clip 10 enter an opened state shown in FIG. 1.

FIG. 13 is a schematic diagram showing the amount of power necessary to pull back the slider with respect to the movement amount by which the slider is pulled back in the endoscope treatment device. The slider 102 is moved (pulled back) toward the proximal end side with respect to the manipulation portion main body 101 from the initial state shown in FIG. 1. The clip 10 is configured such that the amount of power necessary to pull back the slide 102 changes with this movement, as shown in FIG. 13. In FIG. 13, a relative change in the amount of power necessary to pull back the slider in various states such as the initial state of the clip 10 are shown.

The state of the clip 10 is changed from the initial state to a contact state to an overpass state and then to a locking state as an operation of pulling back the slider 102. Hereinafter, the change in the amount of power and the change in the state of the clip 10 will be described in detail.

In the initial state, for example, the diameter expansion portion 72 comes into contact with the stepped portion 68. Thus, the proximal end surface of the pressing tube 31 comes into contact with the distal end support surface 67b, and the pressing tube 31 and the distal end support surface 67b are not separated over at least the depth of the support member 69 in the longitudinal direction.

Next, the clip 10 is turned toward the target tissue T (referred to FIG. 16) inside the body by performing a manipulation of curving a curving portion provided in the endoscope insertion portion while the inside of the body is examined with the endoscope. By pushing the endoscope treatment device 1 in the endoscope, the arm portions 12 and 13 are pressed against the target tissue T.

When the user grasps the manipulation portion 100 and pulls back the slider 102, the first arm portion 12 and the second arm portion 13 are urged toward the inner circumferential surface of the distal end of the pressing tube 31. As a result, the first arm portion 12 is elastically deformed on the side of the second arm portion 13 and the second arm portion 13 is elastically deformed on the side of the first arm portion 12, and thus the distal end of the first arm portion 12 approaches the distal end of the second arm portion 13 (the arm portions 12 and 13 are closed). The helical spring 36 is gradually compressed in the axis Y.

The amount of power by which the slider 102 is pulled back is transmitted to the fracture mechanism 64.

(Action: Contact State from Initial State)

Figure 14:
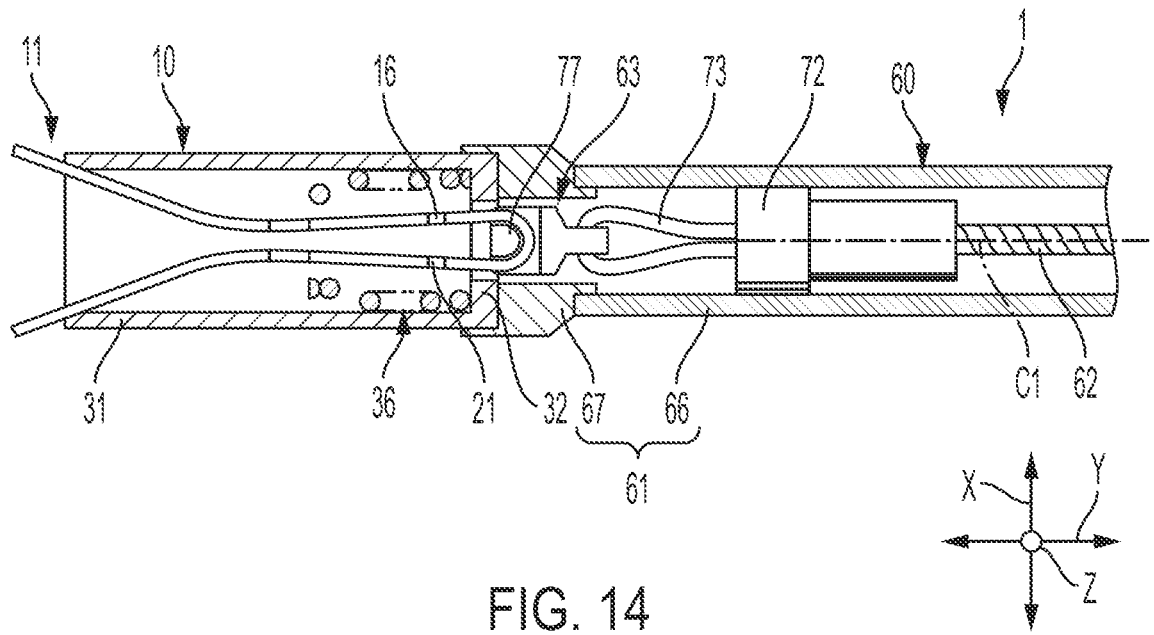
FIG. 14 is a side sectional view schematically showing the endoscope treatment device when the clip unit in FIG. 1 is in a contact state.
Figure 15:
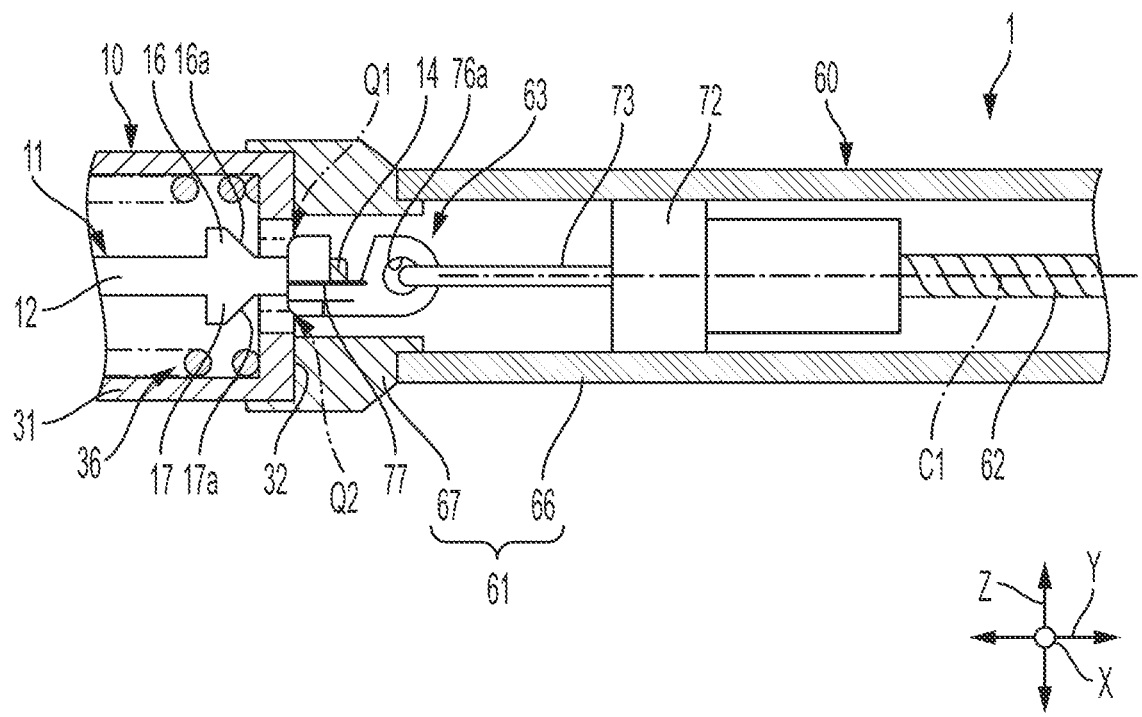
FIG. 15 is a top sectional view schematically showing the endoscope treatment device when the clip unit in FIG. 1 is in the contact state.

When the slider 102 is pulled further back, as shown in FIGS. 7, 14, and 15, the first locked portions 16 and 17 and the second locked portions 21 and 22 enter the contact state with the locking portion 32 of the pressing tube 31. At this time, as shown in FIG. 7, the first locked portion 16 and the first locked portion 17 come into contact with the edge 32a of the pressing tube 31 at the position P1 and the position P2, respectively.

In a region R1 corresponding to the initial state to the contact state, as shown in FIG. 13, the amount of power necessary to pull back the slider 102 increases as the slider 102 is pulled back. The clip 10 is changed from the opened state to the closed state. Since the connection member 63 is disposed inside the pressing tube 31 or the sheath portion 61, the connection member 63 is not rotated with respect to the loop portion 73 and the engagement of the hooking structure 77 and the middle portion 14 is maintained. Since the fracture mechanism 64 does not fracture, the amount of power by which the slider 102 is pulled back can be transmitted to the manipulation wire 62 via the fracture mechanism 64.

When the slider 102 is pushed, the amount of power by which the slider 102 is pushed can be transmitted to the manipulation wire 62.

(Action: Overpass State from Contact State)

Proximal end surfaces 16a and 17a of the first locked portions 16 and 17 are formed to be inclined, as described above. The edge 32a of the locking portion 32 has a circular shape. Therefore, when the slider 102 is pulled further back, the first locked portion 16 receives a perpendicular force from the edge 32a in parallel to a normal line N orthogonal to a tangent line θ of the edge 32a at the position P1 at which the first locked portion 16 comes into contact with the edge 32a of the locking portion 32, when viewed in the axis Y shown in FIG. 18. The perpendicular force moves the first locked portion 16 of the first arm portion 12 in the axis X so that the first locked portion 16 becomes closer to the second arm portion 13.

Figure 16:
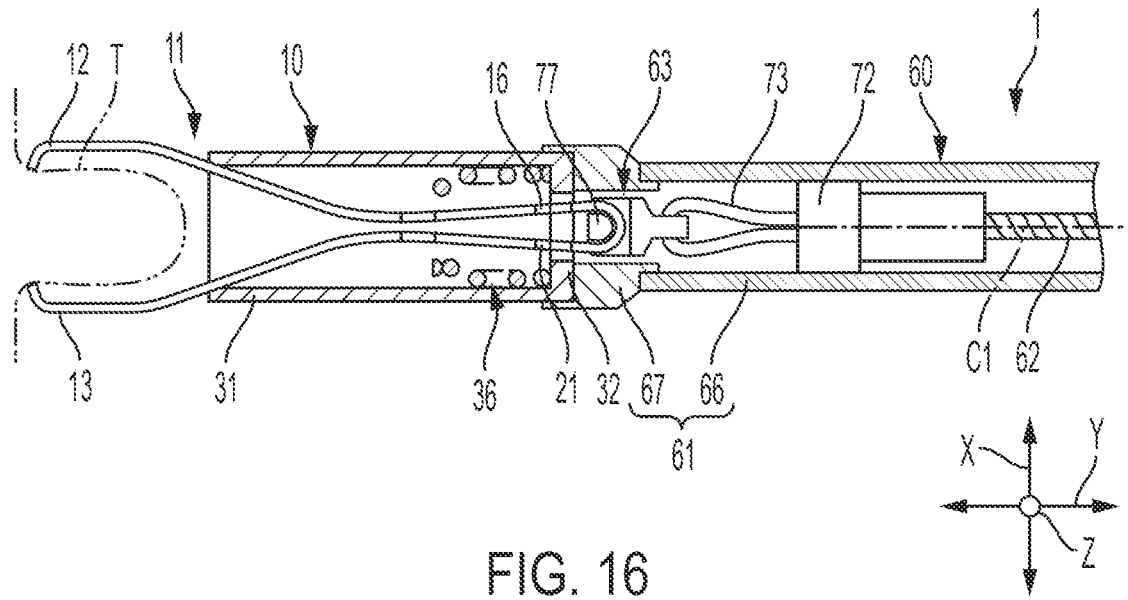
FIG. 16 is a side sectional view schematically showing the endoscope treatment device when the clip unit in FIG. 1 is in an overpass state.
Figure 17:
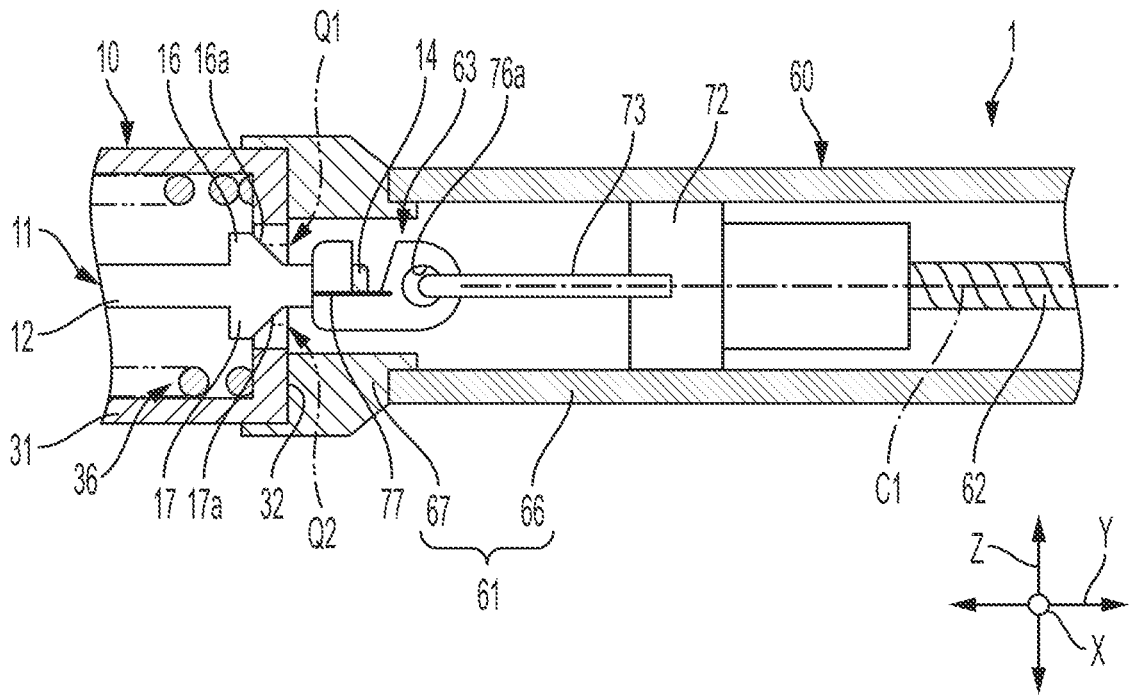
FIG. 17 is a top sectional view schematically showing the endoscope treatment device when the clip unit in FIG. 1 is in the overpass state.
Figure 18:
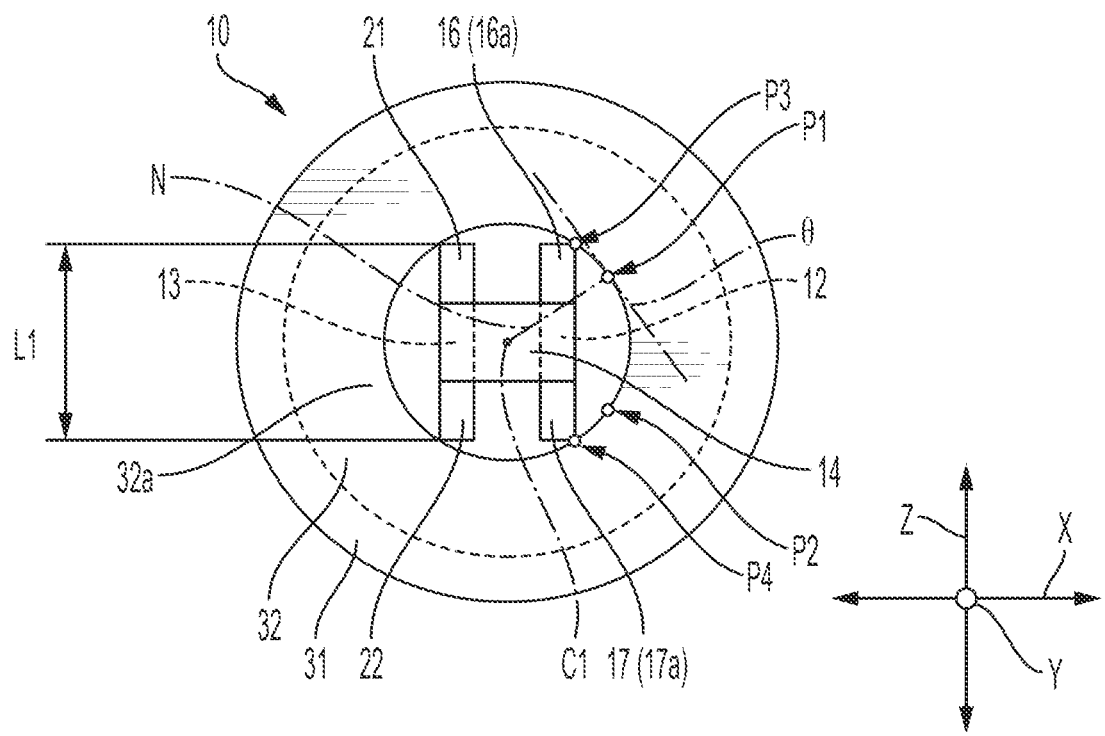
FIG. 18 is a schematic diagram of the clip unit in FIG. 1 in the overpass state when viewed from the proximal end side.

When the pullback manipulation continues, as shown in FIGS. 16 to 18, the first locked portions 16 and 17 come into point contact with the locking portion 32 and the edge 32a of the locking portion 32 with which the first locked portion 16 comes into contact moves from the position P1 to a position P3. Simultaneously, the edge 32a of the locking portion 32 with which the first locked portion 17 comes into contact moves from the position P2 to a position P4. FIGS. 16 to 18 illustrate the overpass state in which the distal end of the proximal end surface 16a of the first locked portion 16 and the distal end of the proximal end surface 17a of the first locked portion 17 come into contact with the edge 32a of the locking portion 32.

Likewise, the second arm portion 13 receives the perpendicular force from the edge 32a of the locking portion 32 and moves in the axis X to become closer to the first arm portion 12. At this time, the middle portion 14 is elastically deformed so that both ends of the middle portion 14 move toward the side of the axial line C1.

By rotating the manipulation wire 62 with respect to the sheath portion 61 in the initial state, the direction of the clip 10 can be adjusted.

In a region R2 corresponding to the contact state to the overpass state, as shown in FIG. 13, there is an increase in the rate of the amount of power necessary to pull back the slider 102 per unit movement amount by which the slider 102 is pulled back (that is, the rate of increase is greater than in the above-described region R1). In other words, while the change of the amount of power characteristic in which the gradient (slope) is relatively gentle is shown in the region R1, a change of the amount of power characteristic in which the gradient (slope) is relatively sharp is shown in the region R2 in which the first locked portions 16 and 17 and the second locked portions 21 and 22 come into contact with the locking portion 32.

That is, the user who pulls back the slider 102 feels that the slider 102 is abruptly heavier in the region R2 than in the region R1 when the user pulls back the slider 102. Thus, the user can easily recognize whether a state in which the user is currently pulling back the slider 102 is in the region R1 or the region R2, in other words, the user can easily recognize whether the slider 102 is being pulled beyond the contact state.

In the region R2, the closed state of the clip 10 is maintained. Since the connection member 63 is disposed inside the sheath portion 61, the engagement of the hooking structure 77 and the middle portion 14 is maintained. The fracture mechanism 64 does not fracture. For example, an amount of power F1 necessary to cause the clip 10 to enter the overpass state, as shown in FIG. 13, is in the range of about 20 N to about 50 N (newtons).

As shown in FIG. 18, in the overpass state, a distance between the positions P3 and P4 of the edge 32a is the same as the length L1 of the first locked portions 16 and 17 described above.

(Action: Re-Gripping)

The clip 10 is elastically deformed. Therefore, when the slider 102 is pushed while the clip 10 is in any state in the regions R1 and R2, the compressed helical spring 36 is stretched. When the pressing tube 31 comes into contact with the distal end support surface 67b, the clip main body 11 is moved toward the distal end side with respect to the pressing tube 31 and the clip 10 enters the initial state shown in FIG. 1. For example, through the manipulation of the curving of the curving portion, the clip 10 is turned toward another target tissue T. Thereafter, by performing the steps in the above-described order, the target tissue T can be re-gripped with the clip 10.

(Action: Locking State from Overpass State)

When the slider 102 is pulled further back from the overpass state, the positions of the first arm portion 12 and the second arm portion 13 with respect to the pressing tube 31 in the axis X and the axis Z are maintained. In this state, the first arm portion 12 provided with the first locked portions 16 and 17 and the second arm portion 13 provided with the second locked portions 21 and 22 are inserted inside the locking portion 32. Then, the first locked portions 16 and 17 and the second locked portions 21 and 22 are moved toward the proximal end side beyond the locking portion 32.

Figure 19:
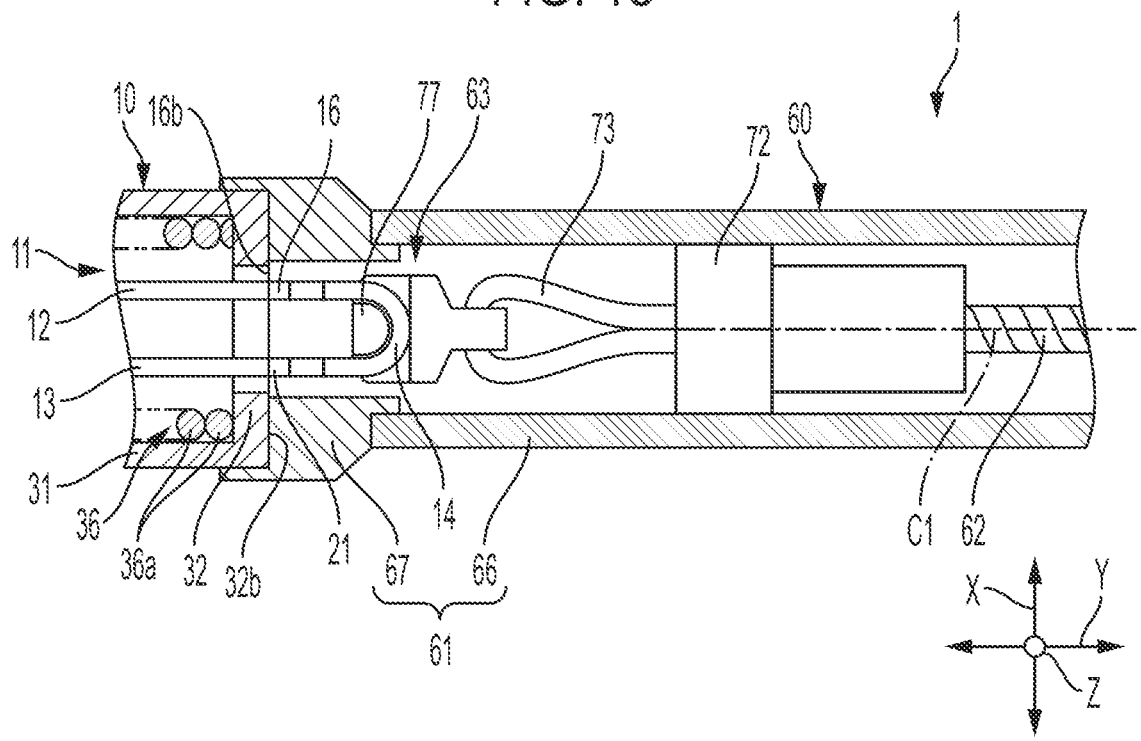
FIG. 19 is side sectional view schematically showing the endoscope treatment device when the clip unit in FIG. 1 is in a locking state.
Figure 20:
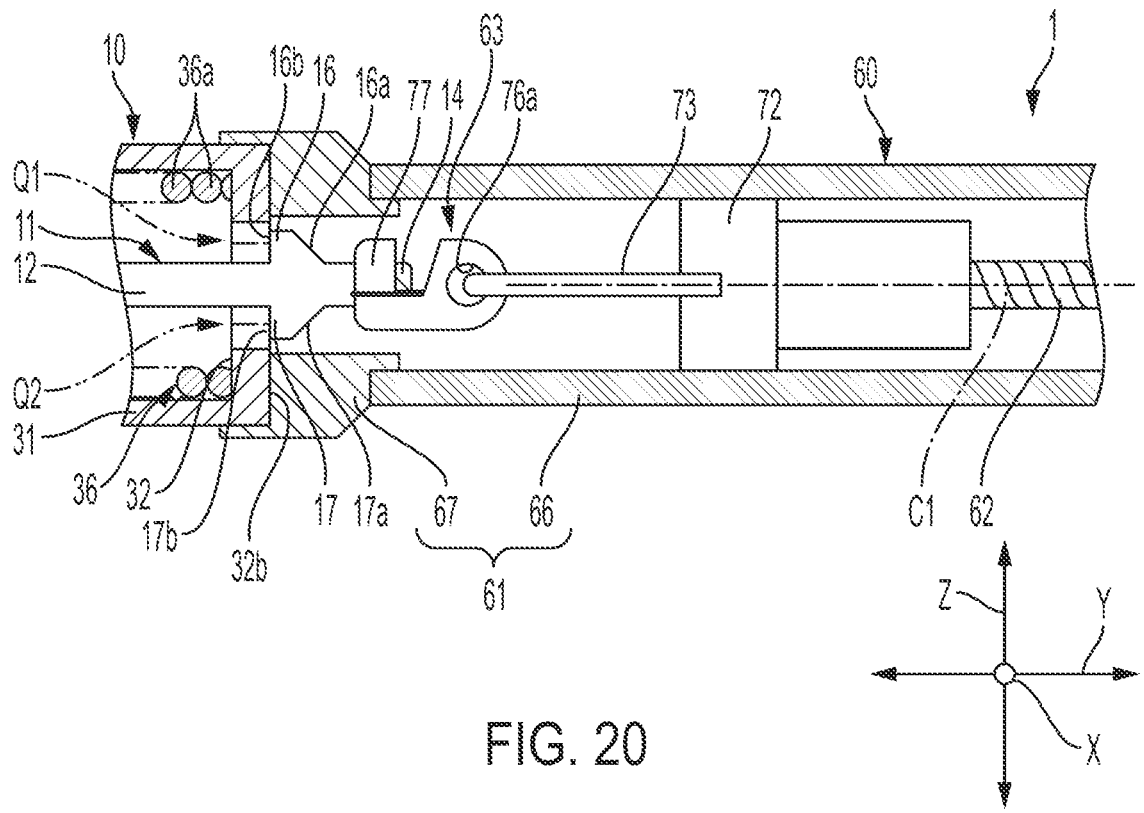
FIG. 20 is top sectional view schematically showing the endoscope treatment device when the clip unit in FIG. 1 is in the locking state.
Figure 21:
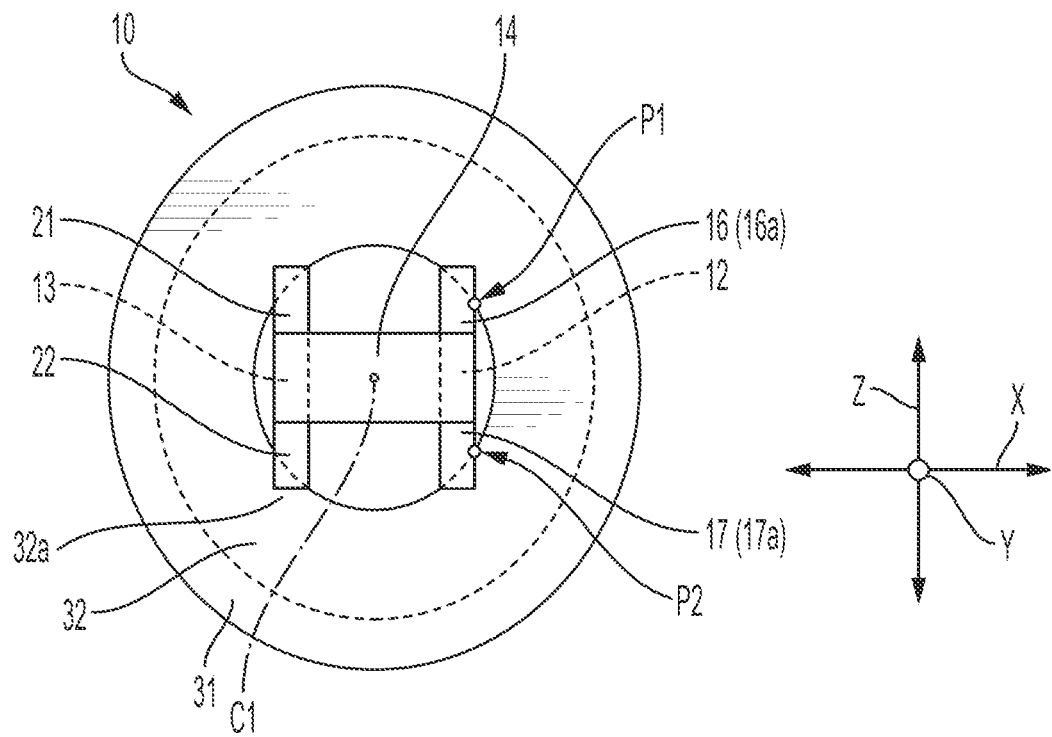
FIG. 21 is a schematic diagram showing the clip unit in FIG. 1 in the locking state when viewed from the proximal end side.

At this time, the arm portions 12 and 13 and the middle portion 14 are not urged from the locking portion 32. Therefore, as shown in FIGS. 19 to 21, the proximal end side of the first arm portion 12 and the proximal end side of the second arm portion 13 are moved in the axis X by the elastic force of the middle portion 14 to be separated from each other. When a force for moving the clip main body 11 toward the proximal end side of the pressing tube 31 is released, the distal end surfaces 16b and 17b of the first locked portions 16 and 17 enter the locking state in which the distal end surfaces 16b and 17b are locked by the proximal end surface 32b of the locking portion 32 (that is, distal end surfaces 16b and 17b are held distally relative to the proximal end surface 32b).

In a region R3 corresponding to the overpass state to the locking state, as shown in FIG. 13, a part of the elastic deformation of the arm portions 12 and 13 and the middle portion 14 is released. Thus, the amount of power necessary to pull back the slide 102 gradually decreases as the slider 102 is pulled back. In the region R3, the closed state of the clip 10 is maintained. Since the connection member 63 is disposed inside the sheath portion 61, the engagement of the hooking structure 77 and the middle portion 14 is maintained. The fracture mechanism 64 does not fracture.

When the clip 10 enters the locking state, as shown in FIGS. 19 and 20, the wires 36a of the helical spring 36 compressed in the axis Y enter a close coiling state in which the wires 36a adjacent in the axis Y are almost touching. When the clip 10 enters the locking state, the distal end surfaces 16b and 17b of the first locked portions 16 and 17 interlock with the proximal end surface 32b of the locking portion 32. Therefore, the movement of the clip main body 11 with respect to the pressing tube 31 toward the distal end side is regulated. That is, a state in which the clip 10 ligates the target tissue T is maintained and the state of the clip does not return to the initial state in which the arm portions 12 and 13 enter the opened state. The clip 10 is fixed in the state in which the arm portions 12 and 13 are closed. In the clip 10, the middle portion 14 protrudes on the proximal end side with respect to the pressing tube 31.

When the first locked portions 16 and 17 and the second locked portions 21 and 22 are moved toward the proximal end side beyond the locking portion 32, the first locked portions 16 and 17 and the second locked portions 21 and 22 may pass over the locking portion 32 by scraping against the locking portion 32 or deforming the locking portion 32. In this case, in order to prevent excessive breakage of the locking portion 32, it is desirable to perform a chamfering process or the like on portions in which the first locked portions 16 and 17 and the second locked portions 21 and 22 come into contact with the locking portion 32.

(Action: Immediately Before Fracture State)

Since the helical spring 36 is in the compressed state, the clip main body 11 may not be moved toward the proximal end side with respect to the pressing tube 31 even if the slider 102 is pulled further back. The locking state of the clip 10 is maintained and not changed. However, when the slider 102 is pulled back, a tensile force acting on the fracture mechanism 64, the manipulation wire 62, or the like gradually increases. In a region R4 shown in FIG. 13, i.e., the region R4 corresponding to the locking state to a state immediately before a fracture state of the fracture mechanism 64 to be described below, as shown in FIG. 13, the closed state of the clip 10 is maintained. Since the connection member 63 is disposed inside the sheath portion 61, the engagement of the hooking structure 77 and the middle portion 14 is maintained. The fracturable member 82 of the fracture mechanism 64 does not fracture.

(Action: Fracture State)

The slider 102 is pulled further back, a manipulation amount of power of the slider 102 reaches a value equal to or greater than a predetermined value, and the tensile force acting on the fracture mechanism 64 exceeds the fracture strength of the fracture mechanism 64. At this time, the fracture mechanism 64 enters the fracture state in which a fracturable member inside the fracture mechanism 64 fractures.

After the fracturable member of the fracture mechanism 64 fractures, the fracture impact is transmitted to the user grasping the manipulation portion 100. That is, the fracture mechanism 64 causes the user to recognize that the clip 10 is fixed in the closed state when the fracturable member of the fracture mechanism 64 fractures. Since the fracture mechanism 64 is provided in the manipulation portion 100, the user can more reliably recognize this impact.

When the user feels the transmitted impact, the user can recognize that the clip 10 has entered the locking state and the ligation state of the target tissue T is maintained. Even when the user pulls the slider 102 further back and brings the slider 102 into contact with the proximal end of the slit 101b of the manipulation portion main body 101, the user can recognize that the clip 10 has entered the locking state.

Since the clip 10 is in the locking state, the manipulation wire 62 is not moved toward the proximal end side.

A region R5 shown in FIG. 13 includes the fracture state and a state in which the slider 102 is pulled further back than the clip is in the fracture state. In the region R5 shown in FIG. 13, the fracturable member of the fracture mechanism 64 fractures, the amount of power necessary to pull back the slider 102 temporarily decreases and then increases as the slider 102 is pulled back. In the region R5, the closed state of the clip 10 is maintained. Since the connection member 63 is disposed inside the sheath portion 61, the engagement of the hooking structure 77 and the middle portion 14 is maintained. The fracturable member of the fracture mechanism 64 fractures.

(Action: Separation of Clip 10)

Thereafter, the clip 10 is separated from the treatment device body 40.

Figure 22:
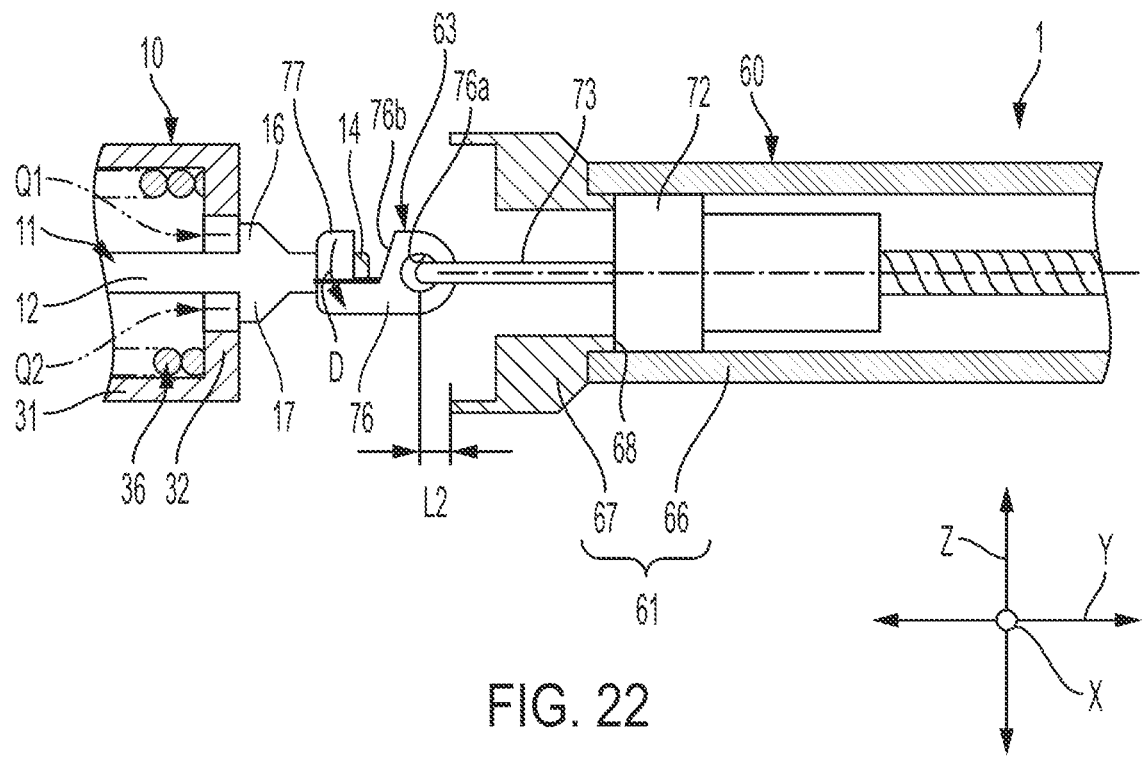
FIG. 22 is a schematic diagram showing another example usage of the endoscope treatment device in FIG. 1.

The order in which the clip 10 is separated from the treatment device body 40 is specifically as follows. That is, when the slider 102 is pushed, the manipulation wire 62 is moved toward the distal end side with respect to the coil sheath 66. As shown in FIG. 22, the distal end surface of the diameter expansion portion 72 comes into contact with the stepped portion 68 and the loop portion 73 protrudes up to the length L2 which is the maximum protrusion amount with respect to the distal end member 67.

Figure 23:
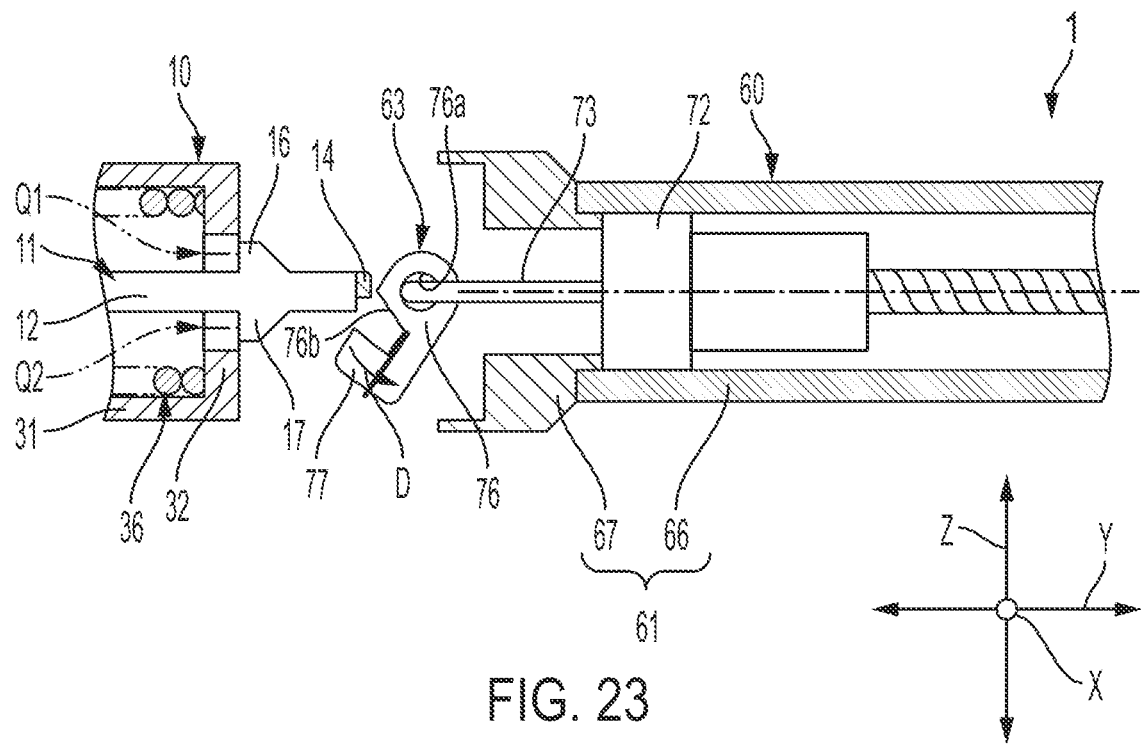
FIG. 23 is a schematic diagram showing still another example usage of using the endoscope treatment device in FIG. 1.

When the connection member 63 protrudes on the distal end side with respect to the distal end member 67, the clip main body 11 and the pressing tube 31 are integrally moved toward the distal end side. Since the connection member 63 is located out of the pressing tube 31, the connection member 63 can be rotated with respect to the loop portion 73. When the slider 102 is pushed and the manipulation wire 62 is moved toward the distal end side, the surface 76b of the connection member 63 comes into contact with the proximal end surface of the middle portion 14 of the clip 10 ligating the target tissue T. As shown in FIG. 23, the hooking structure 77 is guided to the surface 76b and is rotated in the direction D along with the bridge 76, and thus the engagement of the hooking structure 77 and the middle portion 14 is released. Thus, the clip 10 ligating the target tissue T is maintained inside the body.

That is, the closed state of the clip 10 is maintained between the state indicated by the region R5 and a state in which the slider 102 is pushed and the connection member 63 protrudes toward the distal end side with respect to the distal end member 67, as shown in FIG. 22. The engagement of the hooking structure 77 and the middle portion 14 can be released. The fracturable member of the fracture mechanism 64 has been fractured.

(Action: Final Treatment of Technique)

The slider 102 is pulled back and the connection member 63 is accommodated inside the sheath portion 61.

The endoscope treatment device 1 is extracted from the channel of the endoscope. The endoscope insertion portion of the endoscope is extracted from the body of the patient. Thereafter, any other necessary treatment is performed and a series of operations of the technique ends.

While preferred embodiments of the invention have been described and illustrated above, it should be understood that these are exemplary of the invention and are not to be considered as limiting. Additions, omissions, substitutions, and other modifications can be made without departing from the spirit and scope of the present invention. Accordingly, the invention is not to be considered as being limited by the foregoing description, and is only limited by the scope of the appended claims While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A clip device, comprising:
    a tube having an interior volume and at least one open end;
    a clip including a first arm portion and a second arm portion, and wherein the clip is configured to slidably move between a retracted position in which the first and second arm portions are within the interior volume of the tube and a deployed position in which the first and second arm portions protrude from the open end of the tube; and
    an engagement mechanism disposed inside the tube and including a stepped connector and a hooking structure and configured to connect to the clip,
    wherein the stepped connector includes an engaging region connecting two side regions,
    wherein a width of the engaging region of the stepped connector is smaller than a width of a first of the two side regions of the stepped connector,
    wherein the hooking structure includes two lateral surfaces connected by a hook surface, and
    wherein a surface of the engaging region of the stepped connector engages with the hook surface of the hooking structure and each of the two side regions of the stepped connector are adjacent to respective one of the two lateral surfaces of the hooking structure.

2. The clip device according to claim 1, wherein the width of the engaging region of the stepped connector is smaller than a width of a second of the two side regions of the stepped connector.

3. The clip device according to claim 2, wherein the width of each of the first and the second of the two side regions of the stepped connector is 1.5 times to 2 times greater than the width of the engaging region of the stepped connector.

4. The clip device according to claim 1, wherein the two lateral surfaces and the hook surface are located on a distal end portion of the hooking structure and the hooking structure further includes a bridge region, and wherein the bridge has a width that is substantially the same as the width of the engaging region of the stepped connector.

5. The clip device according to claim 4, wherein the stepped connector includes a first seating surface and a second seating surface, the first seating surface contacting an upper surface of the bridge.

6. The clip device according to claim 5, wherein an angle between the first seating surface and the second seating surface is a right angle or an obtuse angle.

7. The clip device according to claim 1, wherein the stepped connector is part of the clip, and wherein the hooking structure is connected to a manipulating wire.

8. The clip device according to claim 1, wherein the hooking structure is a first hooking structure and the engagement mechanism further includes a second hooking structure,
    wherein the second hooking structure includes two second lateral surfaces connected by a second hook surface,
    wherein the stepped connector is a first stepped connector and the engagement mechanism further includes a second stepped connector,
    wherein the second stepped connector includes a second engaging region and two second side regions, and
    wherein the second engaging region of the second stepped connector engages with the second hook surface of the second hooking structure, and each of the two second side regions of the second stepped connector are adjacent to a respective one of the two second lateral surfaces of the hooking structure.

9. The clip device according to claim 8, wherein the hooking structure is part of the clip, wherein the stepped connector is connected to a manipulating wire.

10. The clip device according to claim 1, wherein each of the first and second arm portions includes a locked portion which protrudes therefrom, and the tube includes a locking portion which protrudes from an inner circumferential surface of a proximal end of the tube,
   wherein, when the locked portion interlocks with the locking portion by a first pulling force, a movement of the first and second arm portions with respect to the tube toward a distal end side is regulated, and
   wherein the locked portion can be moved proximally beyond the locking portion by a second pulling force that is larger than the first pulling force by a predetermined amount.

11. An endoscope treatment device for ligaturing a living tissue, comprising:
   a clip unit including a tube having an interior volume and at least one open end and a clip having a first arm portion and a second arm portion, and wherein the clip is configured to slidably move between a retracted position in which the first and second arm portions are within the interior volume of the tube and a deployed position in which the first and second arm portions protrude from the open end of the tube;
   a linear member connected to the clip unit and provided to advance and retract the clip unit; and
   a sheath in which the linear member is inserted so that the linear member is advanceable and retractable;
   wherein the clip unit further includes:
      an engagement mechanism disposed inside the tube and including a stepped connector and a hooking structure, wherein the engagement mechanism is configured to connect the clip,
   wherein the stepped connector includes an engaging region connecting two side regions,
   wherein a width of the engaging region of the stepped connector is smaller than a width of a first of the two side regions of the stepped connector,
   wherein the hooking structure includes two lateral surfaces connected by a hook surface, and
   wherein a surface of the engaging region of the stepped connector engages with the hook surface of the hooking structure and each of the two side regions of the stepped connector adjacent with a respective one of the two lateral surfaces of the hooking structure.

12. The endoscope treatment device according to claim 11, wherein the width of the engaging region the stepped connector is smaller than a width of a second of the two side regions the stepped connector.

13. The endoscope treatment device according to claim 12, wherein the width of each of the first and the second of the two side regions of the stepped connector is 1.5 times to 2 times greater than the width of the engaging region of the stepped connector.

14. The endoscope treatment device according to claim 11, wherein the two lateral surfaces and the hook surface are located on a distal end portion of the hooking structure and the hooking structure further includes a bridge region, and wherein the bridge has a width that is substantially the same as the width of the engaging region of the stepped connector.

15. The endoscope treatment device according to claim 14, wherein the stepped connector includes a first seating surface and a second seating surface, the first seating surface contacting an upper surface of the bridge.

16. The endoscope treatment device according to claim 15, wherein an angle between the first seating surface and the second seating surface is a right angle or an obtuse angle.

17. The endoscope treatment device according to claim 11, wherein the stepped connector is part of the clip, and wherein the hooking structure is connected to a manipulating wire.

18. The endoscope treatment device according to claim 11, wherein the hooking structure is a first hooking structure and the engagement mechanism further includes a second hooking structure,
   wherein the second hooking structure includes two second lateral surfaces connected by a second hook surface,
   wherein the stepped connector is a first stepped connector and the engagement mechanism further includes a second stepped connector,
   wherein the second stepped connector includes a second engaging region and two second side regions, and
   wherein the second engaging region of the second stepped connector engages with the second hook surface of the second hooking structure, and each of the two second side regions of the second stepped connector are adjacent to a respective one of the two second lateral surfaces of the hooking structure.

19. The endoscope treatment device according to claim 18, wherein the hooking structure is part of the clip, and wherein the stepped connector is connected to a manipulating wire.

20. The endoscope treatment device according to claim 11, wherein each of the first and second arm portions includes a locked portion which protrudes therefrom, and the tube includes a locking portion which protrudes from an inner circumferential surface of a proximal end of the tube,
   wherein, when the locked portion interlocks with the locking portion by a first pulling force, a movement of the first and second arm portions with respect to the tube toward a distal end side is regulated, and
   wherein the locked portion can be moved proximally beyond the locking portion by a second pulling force that is larger than the first pulling force by a predetermined amount.

* * * * *